United States Patent [19]
Treco et al.

[11] Patent Number: 5,783,385
[45] Date of Patent: *Jul. 21, 1998

[54] METHOD FOR HOMOLOGOUS-RECOMBINATION SCREENING OF RECOMBINANT-DNA CLONES IN YEAST HOST LIBRARIES

[75] Inventors: Douglas A. Treco, Arlington; Allan M. Miller, Medford, both of Mass.

[73] Assignee: Transkaryotic Therapies, Inc., Cambridge, Mass.

[*] Notice: The term of this patent shall not extend beyond the expiration date of Pat. No. 5,580,734.

[21] Appl. No.: 300,919

[22] Filed: Sep. 6, 1994

Related U.S. Application Data

[63] Continuation of Ser. No. 552,183, Jul. 3, 1990, abandoned.
[51] Int. Cl.$^6$ .............. C12Q 1/68; C12P 19/34; C12N 15/09; C12N 15/81
[52] U.S. Cl. .............. 435/6; 435/91.4; 435/91.41; 435/172.3; 435/320.1
[58] Field of Search .............. 435/6, 172.3, 320.1, 435/91.41, 91.4

[56] References Cited

U.S. PATENT DOCUMENTS

| | | | |
|---|---|---|---|
| 4,745,057 | 5/1988 | Beckage et al. | 435/69.4 |
| 4,818,700 | 4/1989 | Cregg et al. | 435/252.33 |
| 4,889,806 | 12/1989 | Olson et al. | 435/172.3 |
| 4,959,317 | 9/1990 | Sauer | 435/172.3 |
| 5,580,734 | 12/1996 | Treco et al. | 435/6 |

FOREIGN PATENT DOCUMENTS

| | | |
|---|---|---|
| 341215 | 3/1990 | European Pat. Off. |
| 0 416 801 A2 | 9/1990 | European Pat. Off. |
| 199722 | 12/1985 | Nicaragua |
| WO 91/05044 PCT/US91/04926 | 9/1990 7/1991 | WIPO . WIPO . |
| PCT/US91/08679 | 11/1991 | WIPO . |

OTHER PUBLICATIONS

Little, R.D. et al., "Yeast Artificial Chromosomes with 200-to 800-kilobase Inserts of Human DNA Containing HLA, V$_x$5S. amd Xq24–Xq28 Sequences", *Proc. Natl. Acad. Sci., USA*, 86:11598–1602 (1989).

Reeves, R.H. et al., Abstract A2579, "Vectors and Procedures for Construction, Species–Specific Selection, and Mapping of Yeast Artificial Chromosomes" *Cytogenetics & Cell Genetics*, 51: 1064 (1989). Abstract from the 10th International Workshop on Human Gene Mapping.

Huxley et al., "Ordering up big MACs", *Bio/Technol.* 12:586–590, Jun. 1994.

Seed, B., "Purification of Genomic Sequences From Bacteriophage Libraries by Recombination and Selection in vivo", *Nucl. Acids Res.*, 11:2427–2445 (1983).

Lutz, C.T. et al., "Syrinx 2A: An Improved λ phage Vector Designed for Screening DNA LIbraries by Recombination in vivo", *Proc. Natl. Acad. Sci. USA*, 84:4379–4383 (1987).

Kurnit, D.M. and B. Seed. "Improved Genetic Selection for Screening Bacteriophage Libraries by Homologous Recombination in vivo", *Proc. Natl. Acad. Sci., USA* .87:3166–3169 (1990).

Murray, A.W. and Szostak, J.W., "Construction of Artificial Chromosomes in Yeast", *Nature*, 305:189–194 (1983).

Pavan, W.J. et al., "Modification and Transfer Into an Embryonal Carcinoma Cell Line of a 360–Kilobase Human–Derived Yeast Artificial Chromosome", *Mol. Cell. Biol.*, 10:4163–4169 (1990).

Pavan, W.J. and R.H. Reeves, "Integrative Selection of Human Chromosome–Specific Yeast Artificial Chromosomes", *Proc. Natl. Acad. Sci., USA*, 88:7788–7791 (1991).

Pachnis et al., "Transfer of a Yeast Artificial Chromosome Carrying Human DNA from *Saccharomyces cerevisiae* Into Mammalian Cells", *Proc. Natl. Acad. Sci., USA*, 87:5109–5113 (1990).

Cellini et al., "Detection of Homologous Recombination Between Yeast Artificial Chromosomes With Overlapping Inserts", *Nucleic Acid. Res.*, 19(5):997 (1991).

Rothstein, "Targeting, Disruption, Replacement and Allele Rescue: Integrative DNA Transformation in Yeast", *Methods in Enzymology*, 194:281 (1991).

Burke, D.T. et al., "Cloning of Large Segments of Exogenous DNA Into Yeast by Means of Artificial Chromosome Vectors", *Science*, 236:807 (1987).

Compton, J.L. et al., "Insertion of Nonhomologous DNA Into the Yeast Genome Mediated by Homologous Recombination With a Cotransforming Plasmid", *Mol. Gen. Genet.*, 188:44–50 (1982).

Green et al., "Systematic Screening of Yeast Artificial–Chromosome LIbraries by Use of the Polymerase Chain Reaction", *Proc. Natl. Acad. Sci., USA*, 87:1213 (1990).

Little, P.F.R. et al., "Plasmid Vectors for the Rapid Isolation and Transcriptional Analysis of Human β–Globin Gene Alleles", *Mol. Biol. Med.*, 1:483–388 (1983).

Ma, H. et al., Plasmid Construction by Homologous Recombination in Yeast, *Gene*, 58:201–216 (1987).

Stewart, G.D. et al., "Plasmids for Recombination–based Screening", *Gene*, 106:97–101 (1991).

(List continued on next page.)

*Primary Examiner*—Jasemine C. Chambers
*Assistant Examiner*—Scott D. Priebe
*Attorney, Agent, or Firm*—Hamilton, Brook, Smith & Reynolds, P.C.

[57] ABSTRACT

Materials and methods for homologous-recombination screening of r-DNA libraries constructed in a yeast host and methods for homologous-recombination chromosome walking for isolating overlapping DNA sequences for building an extended physical map of a chromosomal region.

29 Claims, 13 Drawing Sheets

OTHER PUBLICATIONS

Pavan et al.,"Generation of deletion derivatives by targeted transformation of human–derived yeast artificial chromosomes", Proc. Natl. Acad. Sci. USA 87: 1300–1304, Feb. 1990.

Traver et al., "Rapid screening of a human genomic library in yeast artificial chromosomes for single–copy sequences", Proc. Natl. Sci. USA 86:5898–5902, Aug. 1989.

Vollrath et al., "Physical mapping of large DNA by chromosome fragmentation", Proc. Natl. Acad. Sci. USA 85:6027–6031, Aug. 1988.

Rothstein, "One–step gene disruption in yeast", Methods in Enzymology 101: 202–210, 1983.

Struhl et al., "High–frquency transformation of yeast: Autonomous replication of hybrid DNA molecules", Proc. Natl. Acad. Sci. USA 76: 1035–1039, Mar. 1979.

Orr–Weaver et al., "Yeast transformation: A model system for the study of recombinantion", Proc. Natl. Acad. Sci. USA 78: 6354–6358, Oct. 1981.

Kurachi et al., "Sumo15A: a lambda phasmid that permits easy selection for and against cloned inserts", Gene 85: 35–43, 1989.

Fincham, "Transformation in fungi", Microbiol. Rev. 53: 148–170, Mar. 1989.

Poustka et al., "Selective isolation of cosmid clones by homologous recombination in *Eschericia coli* ", Proc. Natl. Acad. Sci. USA 81: 4129–4133, Jul. 1984.

Botstein et al., "Yeast: An experimental organism for modern biology", Science 240: 1439–1443, Jun. 1988.

Vijayakumar et al., "Cloning and physical characterization of chromosomal conjugative elements in streptococci", J. Bacteriol. 166: 972–977, Jun. 1986.

Robins, et al. (1981) Transforming DNA integrates into the host chromosome. Cell 23: 29–39.

Gumm et al. (1988) Observations on integrative ransformation in Schizosaccharomyces pombe. Mol Gen Genet 15: 87–93.

Vijayakumasar et al (1986) Structure of a conjugative element in Streptococcus pneumoniae. J. Bacteriol 166: 978–984.

New England Biolabs 1988–1989 Catalog. New England Biolabs Inc., 1988.

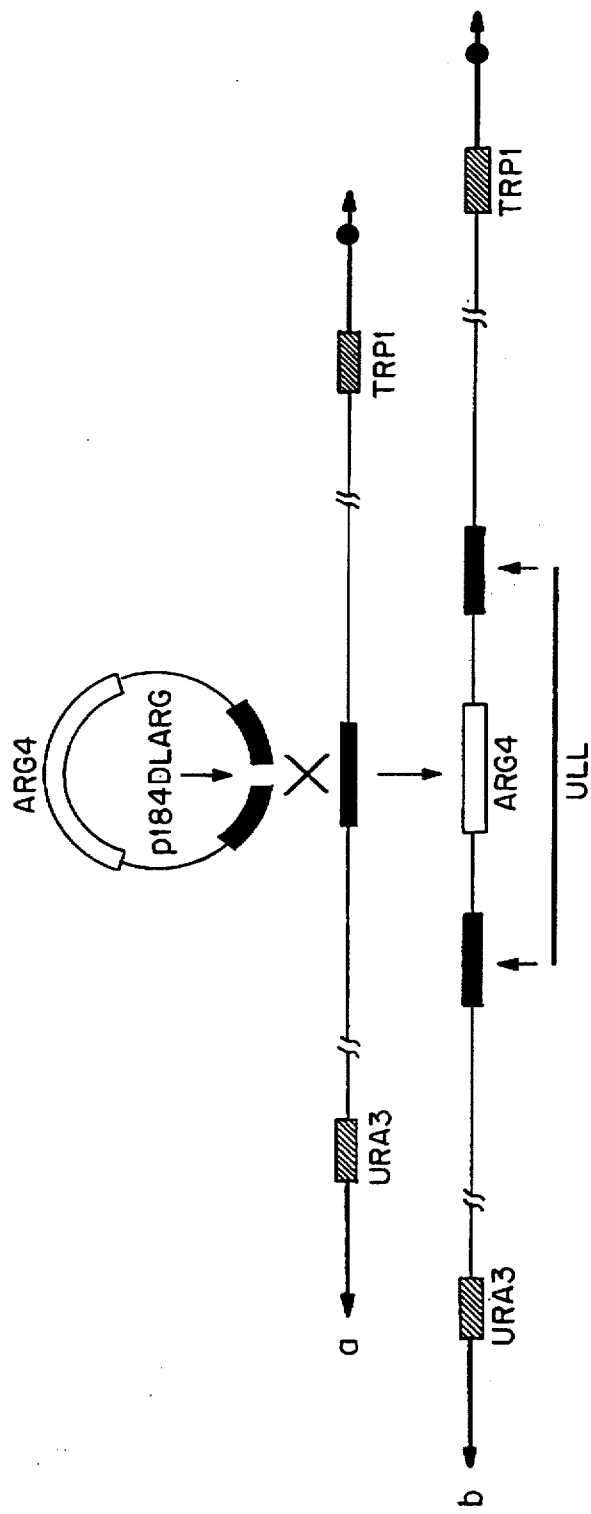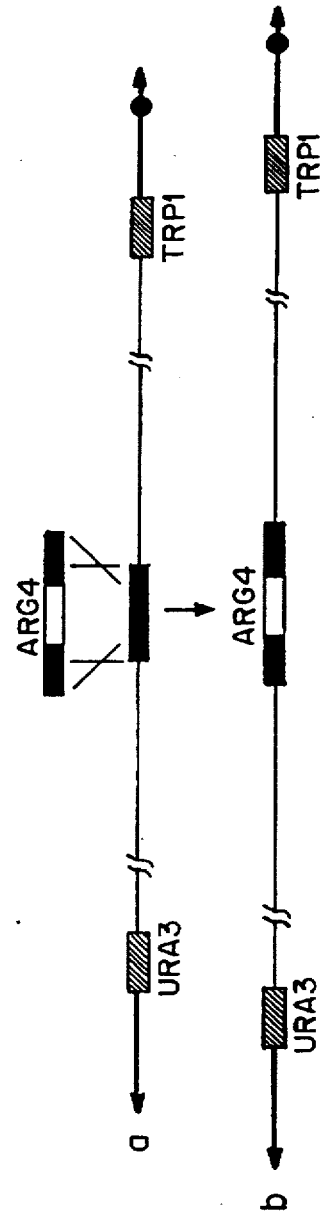

OLIGONUCLEOTIDE

1   AATTCAACAA GCAAGTGCGA TGC

2   GATCCCGGGC CCATGCATCG CACTTGC

SmaI
    AATTCAACAAGCAAGTGCGATGCatgggcccgggatc
        ttaagttgttCGTTCACGCTACGTACCCGGGCCCTAG
                               NsiI  ApaI

3   AATTCACATG TGTCAACTAA ACATAAAACT CGAGGGGATC C

4   GATCTTTTAT AGGGCCCATG CATTACGTAG GATCCCCTCG AG

AATTCACATGTGTCAACTAAACATAAAAACTCGAGGGGATCCtacgtaatgcatggccctataaaagatc
ttaagtgtacacagttgatttgtatttgtatttgAGCTCCCCTAGGATGCATTACGTACCCGGGATATTTCTAG
   HincII       XhoI   BamHI  SnaBI  NsiI    ApaI
                     XhoII

FIG. 6A

The sequences in uppercase letters indicate those bases corresponding to oligonucleotides synthesized *in vitro*. The sequences in lowercase letters indicate those bases filled in *in vitro* using each pair of annealed oligonucleotides. Relevant restriction enzyme recognition sequences are indicated.

OLIGONUCLEOTIDE

5   AATTCGGATC TTTAAACATA AAAGCTTCCG GATCCCG

6   GATCATGCAT GGGCCCGGGA TCCGAAGC

SmaI

AATTCGGATCTTTAAACATAAAAGCTTCCGGATCCCGgcccatgcatgatc
    ttaagcctagaaatttgtatttt<u>cGAAGGCCTAGGGCCCGGGTACGTACTAG</u>
       XhoIIAhaIII     HindIII  BamHI    ApaI NsiI
                                  XhoII

7   GATCCTTTAA ACATAAAAGC TTGGAGATCT AG

8   CTAGGATGCA TGGGCCCAGT ACTAGATCTC CAAG

GATCCTTTAAACATAAAAGCTTGGAGATCTAGtactgggcccatgcatcctag
    ctaggaaatttgtatttt<u>cGAACCTCTAGATCATGACCCGGGTACGTAGGATC</u>
      AhaIII     HindIII BglII  ScaI  ApaI NsiI
                                       XhoII

9A  GATCTGAGCT CAAGGAACAG TACT

9B  AGTACTGTTC CTTGAGCTCA

GATCTGAGCTCAAGGAACAGTACT
    <u>ACTCGAGTTCCTTGTCATGA</u>
      SacI

The sequences in uppercase letters indicate those bases corresponding to oligonucleotides synthesized *in vitro*. The sequences in lowercase letters indicate those bases filled in *in vitro* using each pair of annealed oligonucleotides. Relevant restriction enzyme recognition sequences are indicated.

FIG. 6B

OLIGONUCLEOTIDE

12  GGTCTCTACA GGT<u>T</u>CTGACA TTATT

13  CCGGCGTAGA G<u>A</u>ATCCACAG GACGG

14  CTCCTGATGA <u>C</u>GCATGGTTA CTC

15  GGAAAGAAAT GCA<u>C</u>AAGCTT TTGCC

16  CCGATACCAG GA<u>C</u>CTTGCCA TCC (The underlined base indicates the mutation from the wild-type sequence.)

FIG. 6C

METHOD FOR HOMOLOGOUS-RECOMBINATION SCREENING OF RECOMBINANT-DNA CLONES IN YEAST HOST LIBRARIES

This application is a continuation of application application Ser. No. 07/552,183 filed Jul. 13, 1990, now abandoned, which is incorporated herein by reference in its entirety.

FIELD OF THE INVENTION

The inventions disclosed herein relate to materials and methods for homologous-recombination screening of recombinant-DNA (r-DNA) clones in libraries constructed in eucaryotic hosts.

BACKGROUND OF THE INVENTION

The information required to build living cells, assemble them into complex multicellular organisms, and maintain the function of all living organisms is encoded in the chemical polymer deoxyribonucleic acid, or DNA. The DNA polymer consists of a sequence of chemical units, nucleotides, linked together to form a long strand. Each nucleotide contains a sugar, deoxyribose, and one of four different bases. Two DNA polymer strands are linked together anti-parallel to each other by complementary base pairing, i.e., by hybridization, forming a helix.

DNA is the carrier of the fundamental units of heredity known as genes. A gene is comprised of a few dozen to as many as 2 million bits of information, and provides a cell with the information necessary to perform one out of the many thousands of separate operations that are necessary for life. Chromosomes are the cellular units that contain the genetic material. A typical human chromosome carries 2,000–5,000 separate genes.

Genes were first identified by their role in the inheritance of observable traits and diseases. It is the relationship between a physically definable gene site on a chromosome and a particular disease state that offers hope for understanding the cause of disease and, eventually, a treatment. This hope and the relatively recent development of the recombinant DNA (r-DNA) arts are driving the monumental effort now underway to map the human genome.

Modern r-DNA techniques are based on the gene-splicing technique developed by Cohen and Boyer in 1973. Gene splicing is the process by which two DNA molecules are ligated together. The joining together of pieces of DNA from different parent molecules yields a recombinant DNA or r-DNA molecule. The ligating of a fragment of DNA of interest into DNA vectors such as plasmids, bacteriophages or cosmids produce r-DNA hybrid vectors which become the vehicles by which DNA fragments can be incorporated into a host cell. The DNA fragment to which the vectors have been joined is called a r-DNA clone.

The discovery of restriction enzymes was the basis of the r-DNA arts. A restriction enzyme is an endonuclease that cleaves DNA at sequence-specific sites, thereby creating double-strand breaks. These restriction enzymes are used as sequence-specific biological scissors to fragment DNA before it is combined with a vector.

One of the most common vectors used is the plasmid, a circular DNA molecule that replicates in bacteria and usually carries a selectable marker gene, for example, an antibiotic-resistance gene. In a common technique for manufacture of recombinant vectors, plasmid DNA and foreign DNA are cut with the same restriction enzyme to produce "staggered ends" of complementary base sequences for combining into r-DNA hybrid plasmids. Such staggered ends are called "sticky ends" or cohesive termini because of their ability to combine with complementary sequences produced by the action of the same enzyme on another DNA molecule, e.g., a plasmid and foreign DNA. Cohen and Boyer first created r-DNA hybrid plasmids which contained pieces of foreign DNA (r-DNA clones) inserted into a circular plasmid DNA that had been cut with the same restriction enzyme.

A genomic r-DNA "library" is formed by digesting genomic DNA from a particular organism with a suitable restriction enzyme, joining the genomic DNA fragments to vectors and introducing the r-DNA hybrids into a population of host cells. Complementary DNA (CDNA) is DNA which has been produced by an enzyme known as reverse transcriptase which can synthesize a complementary strand of DNA (CDNA) using a mRNA strand as a template. A r-cDNA library is formed by digesting CDNA prepared using messenger RNA of a particular organism with a suitable restriction enzyme, joining the cDNA fragments to vectors and introducing the r-cDNA hybrids into a population of host cells.

Vectors used to construct r-DNA libraries are typically plasmids or bacterial viruses (bacteriophages) that can replicate in bacteria. Recently, yeast and yeast vectors have been used for the construction of r-DNA libraries in eucaryotic hosts. Host cells are either bacteria or yeast cells depending on the vector used to construct their DNA library.

In producing a r-DNA or r-cDNA library, the pieces of DNA have been fragmented into an unordered collection of thousands or millions of pieces. To isolate a host cell carrying a specific r-DNA sequence, i.e., a specific r-DNA clone, the entire library must be screened. Nucleic acid probes are traditionally employed to screen a r-DNA or r-cDNA library. Nucleic acid probes identify a specific r-DNA sequence by a process of in vitro hybridization between complementary DNA sequences in the probe and the r-DNA clone. A specific r-DNA clone that has been identified and isolated in this manner can contain DNA that is contiguous to the probe sequence. A terminus of the r-DNA clone therefore can be used as a new probe to rescreen the same or another r-DNA, library to obtain a second r-DNA clone having an overlapping sequence with the first r-DNA clone.

By obtaining a set of overlapping r-DNA clones, a physical map of a genomic region on a chromosome may be constructed. This process is called "chromosome walking." Each subsequent overlapping r-DNA clone which is isolated is one step along the chromosome. Because each r-DNA clone also can be studied to determine its physical relationship to a previously mapped genetic function, a series of overlapping r-DNA clones provides a physical map of a chromosome which is, correlated to a map of genetic functions. The chromosomes of the genome can be fragmented into manageable pieces for genetic analysis and pieced back together again step by step to construct linked physical and genetic-function maps.

Genetic polymorphism is the term used to describe the existence of variants of a particular gene that can occur in a population. That is, there are polymorphic versions of a gene, distinguishable by a difference in DNA sequence and often a difference in phenotype. Because the DNA sequences for a genetic locus can be polymorphic, DNA fragments produced by restriction endonuclease digestion of the locus can also be polymorphic. Such polymorphic DNA fragments are called "restriction fragment length polymorphisms" (RFLPs). RFLPs derive from the variability of DNA fragment lengths produced by a restriction enzyme digestion of the same genetic locus from two different samples containing polymorphic variants of the locus. Recent progress in the field of chromosome mapping and identifying the genetic basis of disease in humans has focused on determining if RFLPs and specific disease-causing genes are genetically linked, i.e., physically localized to the same region on one of the 24 human chromosomes. The assignment of RFLP markers to specific positions on chromosomes generates a map, with the positions of the cloned fragments providing landmarks for isolating linked disease-causing genes.

Once a genetic linkage between a RFLP and a disease-causing gene is documented, the next step is to clone DNA between the RFLP locus and the gene itself, often a physical distance of several million base pairs. This cloning process is accomplished by using the RFLP (which is on the order of 1,000 base pairs long) as an in vitro hybridization probe to screen a library of r-DNA clones to isolate much larger fragments of cloned DNA in which all or part of the RFLP sequence is represented.

A library of bacteriophage, bacterial cells, or yeast cells, each carrying a single cloned DNA fragment, is grown as single colonies on the surface of a nitrocellulose or nylon filter (chosen for its high capacity to bind DNA). The bacteriophage or cells are lysed with an alkali and detergent and the DNA is fixed to the filter substrate. The RFLP DNA sequence, which has been labeled, as by introducing radioactive or chromogenic nucleotides into its sequence, is added to a plastic bag containing a suitable hybridization solution, and the DNA-bearing filters. The nucleoside bases on the RFLP DNA strand will randomly collide with exposed bases on the DNA strands fixed to the filter, creating a spectrum of bimolecular interactions which have varying degrees of stability due to varying degrees of identity, or homology, between the RFLP sequence and the clones on the filter. Only a cloned DNA sequence identical to or very similar to the RFLP sequence will hybridize to it and produce a highly stable structure, the result of which gives rise to a dark spot on the filter or on a photographic film sensitive to the radioactive emission from the labeled RFLP DNA. By properly orienting the filter or film over a copy of the library, one can identify the clones that are homologous to the RFLP sequence. The number of clones that would have to be screened is between 50,000 and 1 million, depending on the average r-DNA clone size, which in turn depends on the cloning vector used to construct the library.

The usefulness of any r-DNA clone isolated by the above procedure is that it includes DNA that is contiguous to the RFLP sequence and that is incrementally closer to the position of the sought-after gene than the original RFLP. To get a step closer, a labeled molecule corresponding to the extreme end of the newly isolated r-DNA clone is prepared and used to rescreen the library, with the goal being to isolate r-DNA clones that overlap with the sequences found in the first r-DNA clone and that are incrementally closer to the gene of interest than either the starting RFLP or the first r-DNA clone isolated. This procedure is repeated over and over with the resulting r-DNA clones being used in genetic studies to assess whether they are more closely linked to the gene of interest. This is the painstaking process called chromosome walking, referred to previously. To walk over a distance of 10 million base pairs could require from 100 to 2,000 steps, depending on the r-DNA cloning vector system used. Any approach designed to decrease the work required to take a single walking step would be a major advance.

The number of r-DNA clones which would be required to form a complete library of genomic DNA is determined by the size of the genome and the r-DNA clone capacity of the vector used to clone and propagate the segments of the genomic DNA.

The construction and screening of genomic DNA libraries of organisms with large genomes is labor intensive. The development of vectors having a capacity for large r-DNA clones has helped to reduce the labor involved in screening genomic libraries.

The present invention utilizes as a host cell in which to screen the r-DNA library a cell which has the capacity to engage in genetic recombination substantially exclusively by homologous recombination; that is, exclusively by a pathway that requires a substantial degree of homology between the transforming DNA and the DNA already present within the cell. The term "exclusively" as used in this context is intended to connote the ability to effect homologous recombination without measurable levels of non-homologous recombination under the conditions chosen for transformation and selection of transformed cells. Illustrative of such host cells are the yeast species *Saccharomyces cerevisiae* and *Schizosaccharomyces pombe*.

It is also advantageous in the present invention to utilize host cells and vectors which are capable of retaining and replicating large r-DNA clones from the DNA library. Yeast artificial chromosomes (YACs) endow the above described yeast species with this capacity. The development of YACs has enabled the cloning of segments of DNA in the 300–1,000 kilobase (kb) range, which is a far greater capacity than that achieved with cosmid vectors (approximately 45 kb) or Lambda phage vectors (approximately 15 kb).

Yeast artificial chromosomes are constructed by ligating two vector arms onto the ends of the DNA fragments obtained from restriction enzyme digestion of a genome of interest. The two arms ligated onto either end of the DNA fragment contain all the DNA sequences that are required for chromosomes to replicate in yeast, (ARS, or autonomous replication sequences), to segregate chromosomes to their progeny (CEN, or centromere sequences) and to stabilize chromosome ends (TEL, or telomere, sequences). Large r-DNA ligation products are fractionated from unligated vector arms and used to transform host yeast cells to produce YAC libraries. YACs replicate in the same manner as the host chromosomes and usually are present at one copy per yeast cell. Although YACs are able to accommodate larger r-DNA clone inserts than other known vectors, large numbers of r-DNA clones still have to be screened in a YAC library to identify any single-copy r-DNA sequence within the library. Thus, a requirement for exploiting the use of YAC libraries is the development of screening techniques.

Disclosed herein are novel methods for the physical isolation of r-DNA clones of interest contained as a single copy or low-copy number in eucaroytic vector libraries. Applicants have discovered that the native machinery for homologous recombination which exists within eucaroytic cells can be harnessed for the purpose of screening and isolating desired r-DNA clones in a vector library. These methods are exemplified herein using yeast cells and r-DNA YAC vector libraries.

Yeast cells (e.g., *Saccharomyces cerevisiae*) possess an efficient and precise system for genetic recombination. The natural process of homologous recombination depends on a system of enzymes that search for regions of sequence homology between two DNA molecules (which may be entire chromosomes). Once homology is found, an exchange of information is possible. Plasmids or other vectors carrying r-DNA clones which are naturally-occurring yeast sequences and which are introduced into cells by standard transformation methods are capable of stably integrating into the yeast genome at sites of homology. The efficiency of this process can be increased by up to a thousand-fold by introducing a double-strand break within a DNA sequence on the incoming DNA molecule that is homologous to a sequence resident in the yeast cell. The cloned yeast DNA on the transforming vector is often called the targeting sequence, and the site of integration is the target site. In the specific Examples of the inventions described herein, targeting vectors are used to screen r-DNA YAC vector libraries for a single copy or low-copy number r-DNA sequence.

BRIEF DESCRIPTION OF THE DRAWINGS

FIG. 2 illustrates targeting homologous reciprocal recombination to generate a YAC that is marked for selection.

FIG. 5 illustrates selection by homologous recombination of a r-DNA clone from a r-DNA YAC library using one-step gene disruption.

FIG. 6a contains oligonucleotides used in the construction of YAC arm vectors.

FIG. 6b contains oligonucleotides used in the construction of YAC arm vectors.

FIG. 6c contains oligonucleotides used in the construction of YAC arm vectors.

BRIEF DESCRIPTION OF ATCC DEPOSITS

Figure 1:
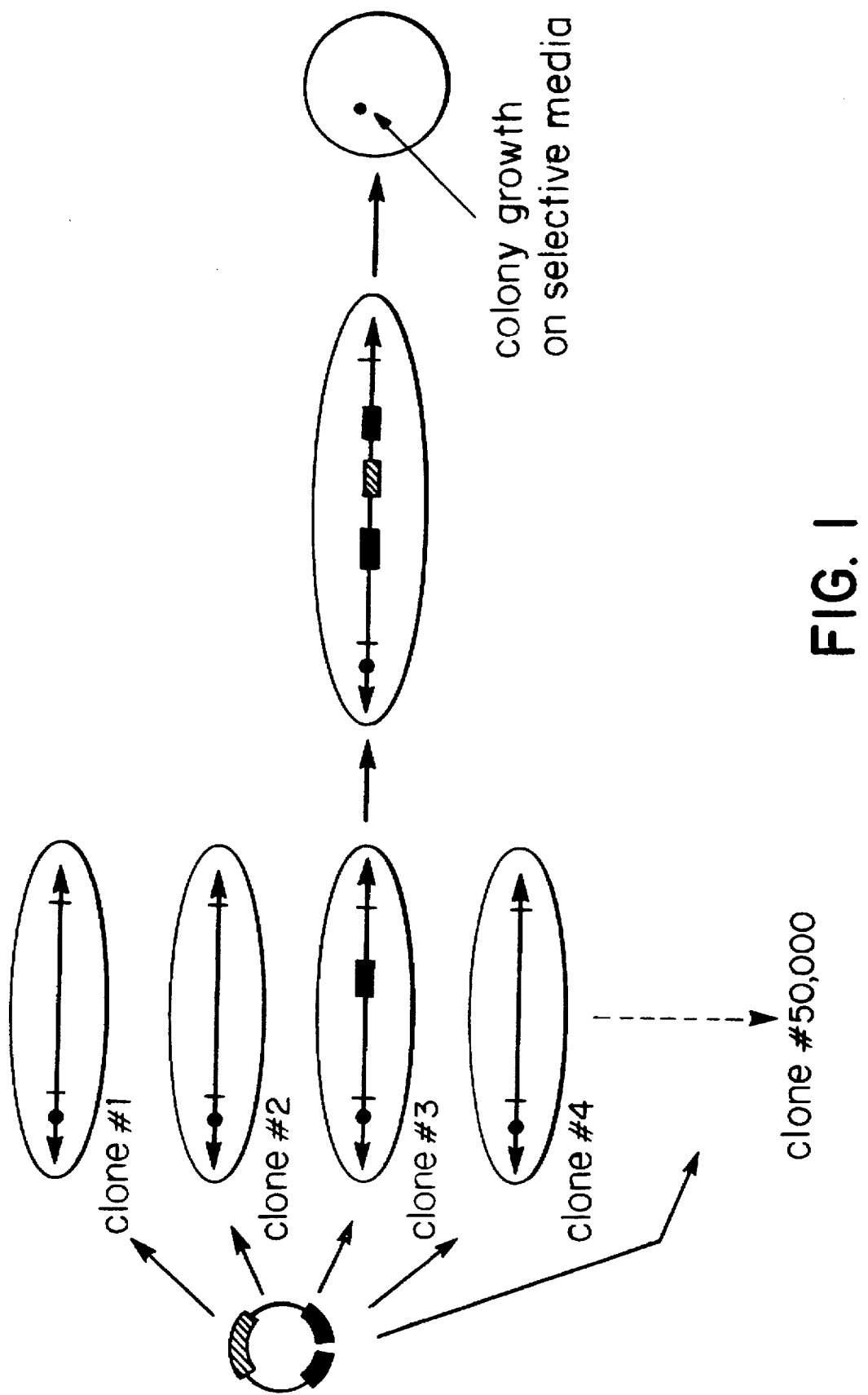
FIG. 1 illustrates the isolation of r-DNA YAC clones by homologous-recombination selection.

The following deposits were made Jun. 28, 1990 at the Americal Type Culture Collection (Rockville, Md.), under the terms of the Budapest Treaty.
1. *Saccharomyces cerevisiae* strain TD7-16d, ATCC No. 74010.
2. Plasmid p184DLARG, ATCC No. 40832, which is contained in *Escherichia (E.) coli* strain K12, substrain MC1061.
3. Plasmid pTKENDA, ATCC No. 40833, which is contained in *Escherichia (E.) coli* strain K12, substrain MC1061.

SUMMARY OF THE INVENTION

Disclosed herein are homologous-recombination methods for screening a recombinant-DNA (r-DNA) library constructed in a eucaryotic host and isolating a desired r-DNA clone sequence, comprising:
a. providing a r-DNA library in a population of host eucaryotic cells, wherein the host eucaryotic cells naturally, by means of genetic manipulation, or by means of genetic engineering undergo genetic recombination between transfected or transforming DNA and DNA resident in the host cell substantially exclusively by a process of homologous recombination;
b. introducing into the population of host eucaryotic cells containing the r-DNA library a targeting DNA molecule which is non-replicating in the eucaryotic host, the targeting DNA molecule having a selectable marker gene for selection in the host cell and a targeting DNA sequence homologous in part to a target r-DNA clone sequence contained in the r-DNA library; and
c. selecting a transformed host cell containing a target r-DNA clone having the selectable marker for the host cell and a portion of the targeting DNA sequence stably incorporated by homologous recombination into the target r-DNA clone.

The specific Examples taught herein to exemplify applicants' inventions are methods for screening a population of yeast cells, each of which contains an artificial chromosome carrying a r-DNA clone insert, and isolating a desired (target) r-DNA clone sequence from this YAC vector library.

A r-DNA library is constructed in yeast artificial chromosomes (YAC) which is contained in a population of host yeast cells. Each cell in the population of host yeast cells usually contains only one chromosome. Such a YAC library might contain 50,000 different r-DNA YAC clones which have to be screened for the presence of the desired r-DNA clone sequence.

A targeting DNA molecule, e.g., a bacterial plasmid, which is non-replicating in yeast is introduced into the population of host yeast cells containing the r-DNA YAC library. (See FIG. 1) The bacterial plasmid has a selectable marker gene that functions in yeast and a first targeting DNA sequence which is homologous in part to a second target r-DNA clone sequence. Preferentially, the targeting plasmid is cut with a restriction endonuclease that introduces a double-strand break within the targeting sequence, thereby linearizing the bacterial plasmid and providing DNA ends which are recombinogenic to stimulate the process of homologous recombination with YAC sequences. Because the plasmid is non-replicating in yeast, stable transformation with the selectable marker can only proceed by homologous recombination. The efficiency of transformation by homologous recombination is increased when the plasmid is cut by restriction enzyme digestion within the targeting DNA sequence homologous in part to the target r-DNA sequence in a YAC.

The host yeast cells are grown under conditions such that only those yeast cells which have been stably transformed, i.e., have had the plasmid and selectable marker stably integrated in the host cell by homologous recombination will be able to grow. In a correctly targeted event, the entire plasmid is stably incorporated contained in the host yeast cell by homologous recombination between the targeting DNA sequence of the plasmid which is homologous to the target r-DNA clone sequence in the YAC. Only those few host yeast cells which contain the desired, target r-DNA clone sequence and have thereby undergone homologous recombination with the targeting plasmid are able to grow under the new growth conditions, due to the introduction of the yeast-selectable marker gene contained on the targeting plasmid.

The vast majority of the population of the host yeast cells containing r-DNA clone sequences which are not homologous to the targeting DNA sequence contained on the plasmid, do not have the plasmid incorporated by homologous recombination and, therefore, do not acquire the marker gene which is essential for growth under the selection conditions. Therefore, it is preferable that any yeast-selectable marker gene which is contained on the incoming targeting plasmid has been deleted entirely or almost entirely from the genome of the host yeast strain which is used for the YAC vector library. This prevents any spurious homologous recombination events between the incoming yeast-selectable marker gene and any other natural yeast genetic loci. If a yeast-selectable marker gene on the incoming targeting plasmid is not deleted, from the yeast genome, but is retained as a mutated, non-functional portion of the yeast chromosome, more positive scores for homologous recombination will have to be screened to ensure that the homologous recombination event has taken place between the targeting DNA sequence on the bacterial plasmid and the desired, target r-DNA clone sequence contained on the YAC.

FIG. 1 illustrates schematically the isolation of r-DNA clones from a YAC vector library by homologous-recombination selection. The plasmid on the far left is introduced into a population of yeast cells (ovals), each of which contains an r-DNA YAC containing a different DNA clone sequence. One clone (clone #3) contains a DNA sequence that is homologous to a sequence carried on the plasmid (black boxes on plasmid and clone #3). Recombination, between these two sequence results in the stable integration of the selectable marker (striped box) carried on the plasmid. Cells with the integrated marker can grow into colonies when plated on appropriate selective media. The arrowheads and filled circles at the ends of the artificial chromosomes represent telomeres and centromere/ yeast replication origins, respectively.

In another embodiment of this method, a yeast-selectable marker gene on the incoming targeting DNA molecule can be a bacterial gene which confers drug resistance to yeast cells, e.g., the CAT or neo genes from Tn9 and Tn903, or bacterial amino acid or amino acid nucleoside prototrophy genes, e.g., the *E.coli* argH, trpC, and pyrF genes.

In another embodiment of the method of homologous-recombination selection of targeted clones from an r-DNA library, the targeting DNA molecule is a linear DNA fragment having a targeting DNA sequence homologous to the target r-DNA clone sequence is introduced into the r-DNA YAC library. The targeting sequence of DNA homologous to the target r-DNA YAC clone sequence exists as two non-contiguous domains, having been disrupted by the insertion of a yeast-selectable marker gene into the targeting sequence. In either embodiment, i.e., the use of a targeting linear DNA fragment or a targeting bacterial plasmid, it is required that the targeting probe is non-replicating in yeast.

Also disclosed herein are methods for isolating physically-contiguous DNA segments from a r-DNA YAC library in order to construct a physical chromosome map, i.e., a method for chromosome walking. In order to walk a chromosome, one first performs the homologous-recombination method for screening and isolating a desired r-DNA clone sequence as described above. Once the first desired r-DNA clone has been obtained, a terminus of the recombinant r-DNA clone insert is subcloned and introduced into a plasmid vector or linear DNA fragment as the targeting DNA sequence as described above. The first r-DNA clone terminus is now a second targeting DNA sequence in a second targeting vector. This new, second targeting plasmid or linear DNA fragment is introduced into host yeast cells containing a r-DNA YAC library. The terminus of the first r-DNA which is contiguous to the first targeting DNA sequence in turn becomes the second targeting DNA sequence. This second targeting DNA sequence should not, have any homology with the first targeting DNA sequence, so that when it in turn is incorporated in a YAC at a point of homology with a second r-DNA clone, the second r-DNA clone selected will have a different terminal DNA sequence. This second terminus subfragment from the second r-DNA clone is used to isolate the next, the third, r-DNA clone. Each successive r-DNA clone is isolated by virtue of its partially overlapping terminal DNA sequences. A series of overlapping clones is obtained by homologous-recombination screening. The process is repeated indefinitely until a large portion of the physical map can be constructed. The successive recovery of terminal r-DNA fragments allows rescreening the same library or a second library for overlapping clones.

In one embodiment of the method of homologous-recombination chromosome walking, the terminal fragments from the r-DNA YAC inserts can be isolated by a plasmid-rescue technique. In this case, the YAC vectors are designed such that the YAC vector arm contiguous to the r-DNA clone insert terminus contains sequences which allow for plasmid replication and selection in a bacterial host. Restriction enzyme digestion of the selected r-DNA clone-containing YAC produces a fragment which starts within the terminus of the r-DNA clone sequence and extends to near the end of the YAC arm. This fragment contains the bacterial plasmid genes which are essential for replication and selection in *E.coli*. Plasmid rescue involves restriction enzyme digestion of the total yeast DNA from the selected yeast clone; ligation of the digested yeast DNA to form monomer circles; and transformation of this ligated DNA mixture into *E.coli*, with the selection for the marker gene in *E.coli*.

For use in conjunction with the plasmid rescue technique, one can design two different r-DNA YAC libraries in different host yeast strains. The two different host yeast strains will have different selectable markers. Each library will utilize a different pair of selectable markers. A set of four YAC arms are designed containing appropriate selectable markers for the two different libraries. Each YAC arm contains a yeast-selectable marker that would be appropriate for the selection of host yeast cells of the other library. Total yeast DNA from cells containing the first targeted r-DNA YAC clone are digested with a restriction endonuclease that separates the sequence conferring replication and stability function in yeast from the region of the cloning vector that allows selection and propagation in bacteria and a selectable marker that functions in yeast. This region is covalently attached to sequences containing the first targeted r-DNA clone terminus. This fragment of the YAC and r-DNA clone terminus contains sequences necessary for replication in bacteria, a selectable marker for a selection in bacteria, and a selectable marker for selection in yeast, along with the first targeted r-DNA clone terminus sequence. This fragment is circularized and amplified in bacteria. This product then becomes the targeting plasmid with which to transform the second r-DNA library, after introducing a double-strand break within the sequence corresponding to the r-DNA clone terminus. The two r-DNA YAC libraries, Library 1 and Library 2, are constructed so that the arms in each are stabilized by a different plasmid vector sequence, with each arm having a unique selectable marker for selection in yeast and a unique selectable marker for selection in bacteria.

DETAILED DESCRIPTION OF THE INVENTION

The Examples below describe the preferred materials and methods for homologous-recombination selection of a targeted r-DNA clone sequence from a r-DNA YAC library. The choice of *Saccharomyces cerevisiae* as a preferred host organism for the selection of r-DNA clones using homologous-recombination is based on its ability to route transforming DNA carrying double-strand breaks into a recombination pathway based virtually exclusively on DNA sequence homology. Homologous-recombination selection of r-DNA clones could be utilized as a selection method in the cells of any organism in which 1) a suitable r-DNA cloning system exists and 2) the cells can be manipulated or induced to perform recombination which is predominantly based on DNA sequence homology, or in which the targeting DNA can be treated in such a manner that it engages in homologous-recombination as its preferred mode of recombination. With these criteria met, one skilled in the r-DNA arts could perform homologous-recombination selection of r-DNA clones from a r-DNA library. Such organisms may include, but are not limited to, *Schizosaccharomyces pombe, Drosophila melanogaster, Homo sapiens, Mus musculus,* and *Autographa californica.*

Unless otherwise noted, methods for plasmid purification, restriction enzyme digestion of plasmid DNA and gel electrophoresis, use of DNA modifying enzymes, ligation, transformation of bacteria, transformation of yeast by the lithium acetate method, preparation and Southern blot analysis of yeast DNA, tetrad analysis of yeast, preparation of liquid and solid media for the growth of *E.coli* and yeast, and all standard molecular biological and microbiological techniques can be carried out essentially as described in Ausubel et al. (Ausubel, F. M. et al., Current Protocols in Molecular Biology, Greene Publishing Associates and Wiley-Interscience, New York, 1987).

For near-complete (>99%) coverage of the human genome, an r-DNA YAC library with an average clone size of 300 kb would consist of approximately 50,000 members (Maniatis, T. et al., Molecular Cloning—A Laboratory Manual, pg 271, Cold Spring Harbor Laboratory Press, Cold Spring Harbor, N.Y., 1982). In order to isolate sequences that are represented only once in such a library, the ratio of targeted to non-targeted events should approximate or exceed 50,000 to 1, for at this ratio one incorrect (non-targeted) clone will be isolated for every correct clone. On average, however, sequences in this library will be represented 3–5 times, and a ratio of 10,000–17,000 to 1 would be adequate. Non-targeted events result from recombination between the targeting plasmid and regions of homology in the yeast genome, and can be minimized by decreasing the total amount of such homology. For purposes of the inventions described in the Examples below and claimed herein which require the use of homologous recombination for the selection of a targeted r-DNA clone from a r-DNA YAC library, it has been determined that the selectable marker gene(s) chosen for the targeting vector should not normally be present in the host yeast genome or should be deleted from its normal chromosomal position in the host yeast strain. Without this modification of the host strain, recombination events between the selectable marker and the yeast genome would occur at an unacceptably high rate, even when the targeting is directed by a double-strand break that is made in a region of the plasmid that has no homology with the yeast genome.

Orr-Weaver et al. (*Proc. Natl. Acad. Sci. USA*, Vol. 78, No. 10, pp. 6354–6358, October 1981) showed that a plasmid carrying the yeast LEU2 gene results in leu+ transformants at a frequency of 1.4–1.7 per µg of DNA when a double-strand break was made in the pBR322 portion of the plasmid. This is 1/10 of the frequency at which leu+ transformants arose when targeting was directed to the LEU2 gene by a double-strand break in LEU2 sequences (12–17 per µg of DNA). Similarly, when a HIS3 containing plasmid was cut within pBR322 sequences, his+ transformants appeared at 1/60 of the rate observed when the same plasmid was cut within HIS3. In both cases, the non-targeted prototrophs were demonstrated to be the result of recombination between the plasmid and the chromosomal leu2⁻ and his3⁻ mutant genes. Thus, screening a library for one clone out of 50,000 by homologous recombination without deletion of the chromosomal LEU2 gene would be expected to yield 5,000 leu+ transformants which arise through homologous recombination with the yeast genome when the targeting plasmid carries LEU2, even if a double-strand targeting break is made in another part of the plasmid. The results suggest, however, that deleting the chromosomal copies of LEU2 or HIS3 would eliminate virtually all of the nontargeted events.

The need for chromosomal deletions for the purposes of the inventions claimed and described in the Examples below was quantified as follows: A plasmid carrying the yeast ARG4 ("target") and URA3 ("marker") genes was transformed into a mixture of yeast cells after making a double-strand break at the unique BclI site in the ARG4 sequence. All of the cells in the mixture had homology to URA3, but only 1 in 1,000 or 1 in 10,000 had homology to ARG4. This type of dilution experiment measures the relative frequencies of targeted and non-targeted events. For example, using 1 µg of DNA and a 1 to 1,000 dilution, the isolation of 5 yeast colonies by homologous recombination at ARG4 indicates that 5,000 cells were theoretically capable of a targeted event, but only 5/5,000 cells actually had the necessary homology at ARG4. The targeting frequency is therefore equivalent to 5,000 targeted events per µg in an undiluted culture. If, in the same experiment, 5 colonies were isolated that were independent of homology at ARG4 (recombination at URA3 or elsewhere, non-targeted events), the frequency of these non-targeted events is 5 per µg, and the ratio of targeted to non-targeted events in this experiment would be 1,000 to 1.

For the 1 in 1,000 dilution, 78 targeted transformants were isolated (by recombination with ARG4; equivalent to 78,000 targeted events) and 17 by recombination elsewhere (non-targeted events). At a dilution of 1 in 10,000, four targeted events (equivalent to 40,000 targeted events) and seven non-targeted events were isolated. The ratio of targeted to non-targeted events is thus (78,000+40,000) divided by (17+7), or 4,917 to 1. This ratio would lead to approximately 10 incorrect events for every one correct event when screening a library for a sequence present on 1 in 50,000 YACs, which is several-fold too high to be generally acceptable, although the use of URA3 as a targeting marker is clearly preferred over the use of the LEU2 or HIS3 markers previously used in targeting studies (Orr-Weaver et al., 1981). 84% (16 of 19 analyzed) of the non-targeted events were in fact due to recombination between the URA3 marker on the plasmid and the chromosomal ura3⁻ locus. If there were no homology between the targeting plasmid and the chromosomal ura3⁻ locus, then the non-targeted events resulting from homology at the ura3⁻ locus are removed from the analysis, then the ratio increases to 30,729 to 1. At this ratio, a sequence represented 3 times in 50,000 YACs would be correctly targeted 1.8 times for every one non-targeted event. This ratio would also result in the favorable ratio of one correct event for every 1.6 incorrect events when screening a library for a sequence present on only 1 in 50,000 YACs.

These results indicate that the selection of a targeted clone from an r-DNA YAC library will be feasible and efficient, but only in host yeast cells that carry no homology with selectable markers present on targeting vectors.

A second source of non-targeted events would arise from homologous recombination between the bacterial plasmid origin of replication or drug resistance marker on the targeting plasmid, and homologous sequences on the YAC vector arms used to construct the r-DNA library. This homology can be minimized by constructing the targeting vector using a drug resistance marker that is not part of the YAC vector, and by, using a bacterial plasmid origin of replication that is divergent from or non-homologous to the origin present on the YAC vector arms. The results also place the frequency of non-homologous recombination at approximately 0.003% (1 in 30,729), consistent with the requirements of the invention described in this application. It was possible to select yeast cells carrying homology to the targeting vector even when only 1 in 10,000 of the cells transformed had such homology. In fact, at this dilution targeted events were isolated multiple (four) times, indicating that a clone represented once in a library of 40,000 clones could be isolated.

The general scheme for selection of a targeted r-DNA clone from a r-DNA YAC library is shown in FIG. 2. FIG. 2 illustrates the integration of a targeting plasmid (p184DLARG) carrying a selectable marker (the yeast ARG4 gene; open box) and a segment of DNA that is homologous to a sequence in the r-DNA YAC library (the targeting sequence; solid arcs on plasmid). The thin lines represent an insert of human DNA propagated as a yeast artificial chromosome (YAC). The solid black box is the target sequence, a sequence of r-DNA constituting a portion of an r-DNA clone found in the library that is homologous to the targeting sequence. The remaining portions of the r-DNA YAC are comprised of the YAC vector arms: the thick lines represent plasmid vector sequences for replication and selection in bacteria. The shaded boxes represent genetic markers used for selection in yeast (yeast selectable markers URA3 and TRP1). The solid arrowheads and circle represent telomeres (TEL) and a centromere/yeast replication origin (CEN/ARS), respectively. a depicts the targeting molecule aligning with the target sequence on the r-DNA YAC. b depicts the product of homologous recombination between the targeting and target sequences. The targeting plasmid has been cut uniquely in the targeting sequence, at the site corresponding to the vertical arrow in the target sequence. ULL indicates the unit length linear restriction fragment that results from duplication of the target sequence (and the restriction site) on the YAC.

EXAMPLE I

SELECTION BY HOMOLOGOUS-RECOMBINATION OF A TARGETED r-DNA CLONE FROM AN r-DNA YAC LIBRARY

Plasmid pYAC4 (ATCC #67380) was used to construct a library of human genomic DNA. Human DNA was isolated from white blood cells (D. Burke, Ph.D. Thesis, Washington University, St. Louis, Mo., 1988), partially digested with EcoRI and ligated to pYAC4 arms digested with EcoRI and BamHI.

The ligation mixture was then used to transform one of two host strains, 131-10c or IV-16d using the spheroplast method (Burgers, P. M. J. and Percival, K. J. (1987) Analytical Biochemistry,. 163:391–397). (The construction of host strains 131-10c and IV-16d with the appropriate marker deletions were described in Example III below.) Since the pYAC4 vector carries the yeast selectable markers TRP1 and URA3, transformants can be selected for by growth on plates lacking tryptophan and uracil. 11,625 YACs with an average size of 190 kb (0.73 human genome equivalents) are individually grown in the wells of 96-well microtiter plates; 0.1 ml was taken from each well and pooled in three subpools of approximately 4,000 clones each. For each subpool, an equal volume of 30% glycerol was added and the subpool was aliquoted and frozen at −70° C.

For a library comprising 73% of one genome, and assuming equal representation of all clones, the probability that it contains any one specific human DNA sequence is just over 0.5. The probability that one of six different fragments of DNA is represented in the library is $1-(0.5)^6$, or 0.98.

Figure 3:
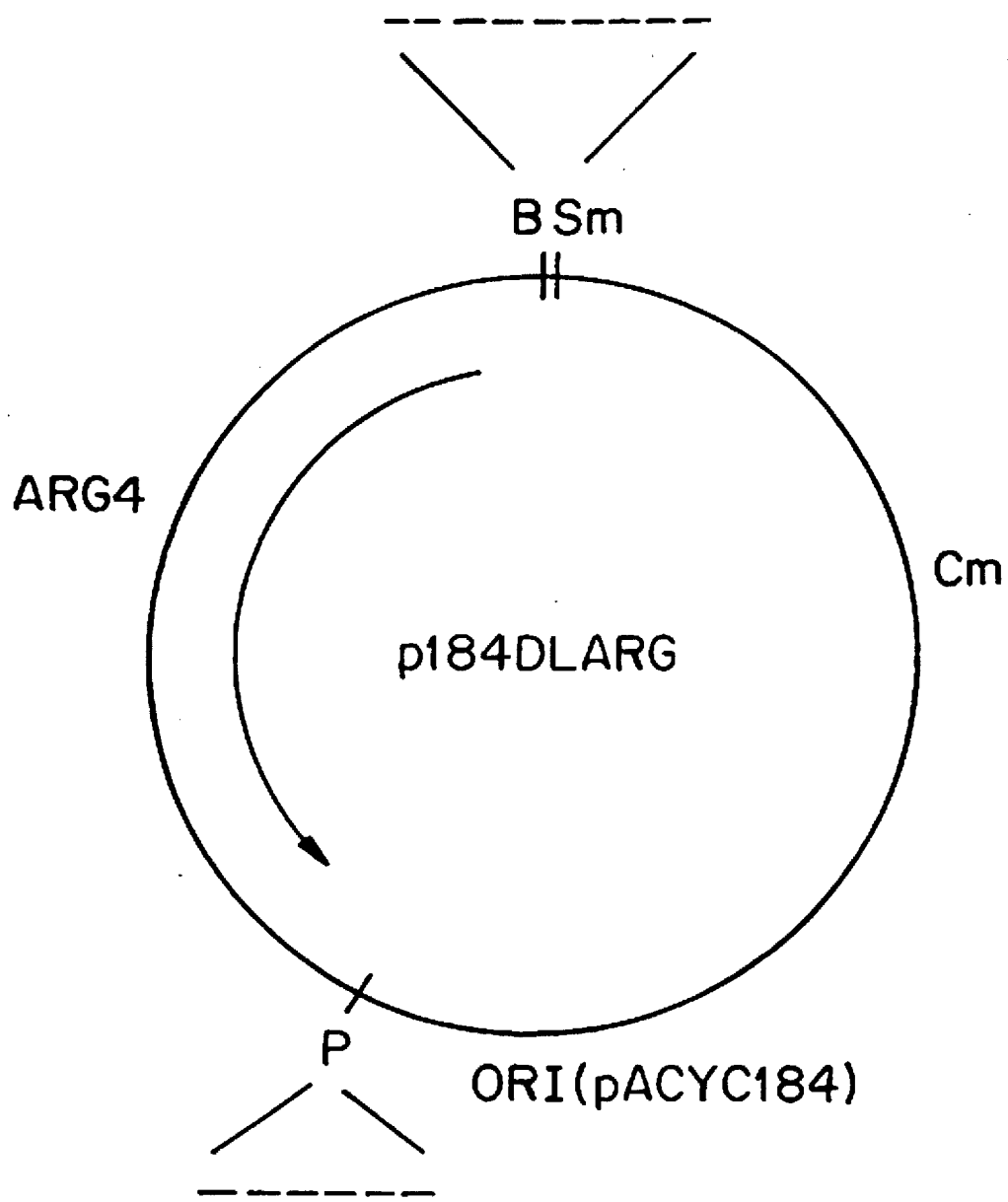
FIG. 3 is a map of plasmid p184DLARG.

Six human genomic DNA fragments were cloned into the targeting plasmid p184DLARG. The construction of the targeting plasmid p184DLARG is described below and illustrated in FIG. 3. It carries the yeast ARG4 (Beacham, I. R., Schweitzer, B. W., Warrick, H. M., and Carbon, J. (1984) Gene 29:271–279) gene as a selectable marker, and its bacterial origin of replication is derived from pACYC184 (Chang, A. C. Y. and Cohen, S. N. (1978) Journal of Bacteriology 134:1141–1156.) which shares only limited sequence homology to the pBR322 origin used on pYAC4. The entire chromosomal copy of ARG4 has been deleted in the library host strains IV-16d and MGD131-10c. The 2.2 kb BclI-ClaI fragment from pACYC184 (Chang, A. C. Y. and Cohen, S. N., 1978) containing the p15A origin of replication and the chloramphenicol resistance gene was ligated to BamII-AccI digested pMLC28 (a derivative of pSDC12 carrying the pUC18 multiple cloning site; Levinson et al., 1984; plasmid pUC18 (ATCC #37253) can substitute for pMLC28 in the construction of p184DLARG described here). BamHI and AccI cut this plasmid one time each, in the polylinker. The ligation mixture was digested with SacI and HindIII, which cut in the pMLC28 polylinker, and the digested DNA was treated with T4 DNA polymerase to generate blunt ends. The DNA was ligated under dilute conditions to promote circularization, and the ligation mix was treated with the restriction enzyme AvaII (to linearize any parental molecules) prior to transformation into bacteria. One plasmid p184DL, carrying only the sequences contained within the larger of the two BclI-ClaI fragments of pACYC184 and a permuted version of a portion of the pMLC28 polylinker was identified. Plasmid pHpa5 (provided by N. Schultes and J. Szostak; Department of Molecular Biology, Massachusetts General Hospital, Boston, Mass. 02114) carries the ARG4 gene as a 2.0 Kb HpaI fragment inserted into the HincII site of pMCL12 (a derivative of pSDC12 carrying the pUC12 multiple cloning site; Levinson et al., 1984). This plasmid was cut at the PstI and SmaI sites flanking the ARG4 insert, and the ARG4 fragment was ligated to PstI-SmaI cut p184DL. A plasmid carrying a single copy of the ARG4 gene inserted in the orientation shown in FIG. 3 was isolated and designated p184DLARG. FIG. 3 is a map of plasmid p184DLARG: B: BamHI; Sm: SmaI; P: PstI; ARG4: yeast ARG4 gene (arrow indicates direction of transcription); Cm: chloramphenicol resistance gene; ORI (pACYC184): Origin of replication from pACYC184; ------: targeting sequence cloning site.

Genomic fragments for tyrosine hydroxylase (chromosome 11), metallothionein II pseudogene (chromosome 4), anonymous DNA markers D16S3 and D16S37 (chromosome 16), and a 1.9 kb HindIII fragment 5' to the epsilon globin gene (chromosome 11) were subcloned into p184DLARG and used for selection of clones by recombination from a YAC library. With the exception of the tyrosine hydroxylase gene fragment, all of the fragments were blunt ended by treatment with T4 DNA polymerase and ligated to SmaI cut p184DLARG. The tyrosine hydroxylase gene fragment was cloned into the BamHI site of p184DLARG. A 1.3 kb HpaI-BamHI fragment from the 5' end of the beta globin gene (chromosome 11) was blunt-end ligated to the same 2.2 kb BclI-ClaI fragment used to construct p184DLARG. The beta- and epsilon-globin fragments are 1.3 and 1.9 kb fragments, respectively, from the human beta-hemoglobin locus on chromosome 11. The beta-globin fragment (ATCC #39698) was subcloned from pHU5'beta (Treco, D., et al., Mol. Cell. Biol., 5:pp 2029–2038, 198), and includes sequences from positions 61,338 (HpaI site) through 62,631 (BamHI site) in the Genbank HUMHBB sequence. This fragment includes the 5' end of the human beta-globin gene. The AvaII site at Genbank map position 62,447 was used to introduce a double-strand break for targeting, leaving 1.1 and 0.18 kb of homology on either side of the break. 5' epsilon-globin is a HindIII fragment and includes sequences centered approximately 15 kb 5' to the epsilon-globin gene (ATCC #59157), from positions 3,266 through 5,172 in the Genbank HUM-HBB sequence. The ApaI sites at map positions 4,361 and 4,624 were used to create a 0.26 kb double-strand gap for targeting, leaving 1.1 and 0.55 kb of homology on either side of the gap.

Properties of the remaining four genomic DNA fragments are as follows: tyrosine hydroxlase (chromosome 11; 2.3 kb BamHI fragment; ATCC #59475; double-strand break made with HindIII, 0.6 kb from end); metallothionein pseudogene (chromosome 4; 2.8 kb HindIII-EcoRI fragment; ATCC #57117; double-strand break made with NdeI, 0.4 kb from end); anonymous DNA marker D16S3 (chromosome 16; 1.5 kb HindIII fragment; ATCC #59447; double-strand break made with ApaI, 0.75 kb from end); D16S37 (chromosome 16; 2.3 kb HindIII fragment; ATCC #59189; double-strand break made with ApaI, 0.95 kb from end).

Each targeting plasmid was linearized with a restriction enzyme that cuts within the human DNA (the targeting DNA) and 20 µg of digested DNA was used to transform the pooled library. Equal volumes of the three library subpools were mixed and inoculated into CM -ura -trp medium containing 40 µg/ml each of kanamycin and ampicillin. This culture was grown overnight at 30° C. with vigorous shaking and harvested at a density of $1.86 \times 10^7$ cells/ml. The cells were transformed using the lithium acetate method (Ausubel et al. op cit 1987 Supplement 5). 20 µg of plasmid cut within the human DNA was used to transform $7 \times 10^8$ cells in a volume of 0.2 ml, and the entire transformation mix was spread onto the surface of eight selective plates (complete minimal media lacking uracil, tryptophan, and arginine) and incubated at 30° C. for 3–7 days.

Transformants were analyzed by restriction enzyme digestion and Southern hybridization analysis. DNA was prepared from each of the candidates and digested with the same enzyme used to linearize the targeting plasmid. The southern blot was probed with 32p radiolabelled ARG4 DNA. Homologous integration events are identified by hybridization to a single band of exactly the same size as the linearized transforming DNA molecule [the "Unit Length Linear" band (ULL); FIG. 2]. A ULL can only be generated if integration occurs into a DNA sequence that contains the restriction enzyme site in question, and contains enough homology surrounding that site to allow the re-synthesis (by repair) of the restriction enzyme site on the targeting plasmid. Candidates that display a ULL are assumed to be homologous integration events and are subjected to further analysis. Unit length linears were seen for 6 of 21 epsilon-globin candidates analyzed and for 3 of 14 beta-globin candidates.

Figure 4:
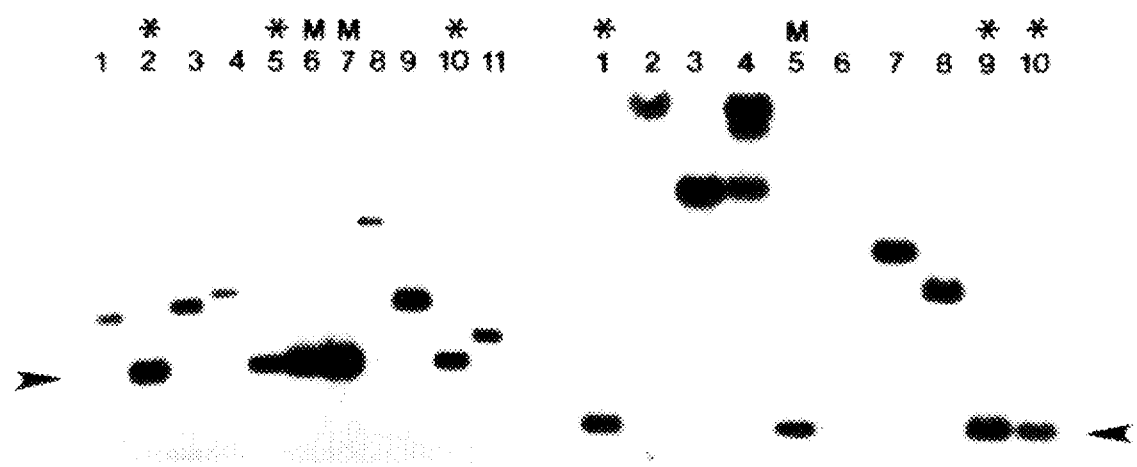
FIG. 4 is a restriction enzyme and Southern blot analysis of clones selected by targeting with human epsilon- and beta-globin sequences.

FIG. 4 is a restriction enzyme and Southern blot analysis of clones selected by targeting with human epsilon- and beta-globin sequences. In the left panel, DNA from nine clones selected as arg were digested with AvaII (the enzyme used to make, the double-strand break in the beta-globin targeting sequence). In the right panel, DNA from nine clones selected as arg+ were digested with ApaI (the enzyme used to make the double-strand break in the epsilon-globin targeting sequence). The asterisks identify clones correctly selected by homologous recombination. The lanes marked M were loaded with purified beta-globin targeting plasmid digested with AvaII (left panel), or purified epsilon-globin targeting plasmid digested with ApaI (right panel). The size of this marker fragment is identical to the size predicted for correctly targeted events. The arrowheads indicate the fragment size predicted for correctly targeted events, 5.6 kb in the left panel and 6.2 kb in the right panel. Hybridization was with $^{32}P$ labeled ARG4 DNA.

Three each of the beta- and epsilon-globin positives were further analyzed by CHEF gel electrophoresis (Chu, G., Vollrath, D., and Davis, R. W. Science 234; pp 1582–1585 (1986), and restriction enzyme and Southern hybridization analysis, probing with epsilon- or beta-globin DNA as appropriate. This analysis demonstrated that all six YACs are identical and carry both beta- and epsilon-globin DNA, as would be expected since these two genes lie only 40 kb apart on human chromosome 11. In all six YACs the ARG4 DNA has integrated onto a YAC of 190 kb and the p184DLARG constructs have integrated as predicted into the homologous DNA within the globin locus.

Homologous recombination has been successfully used to isolate unique genes from a r-DNA YAC library. The YACs isolated encompass the entire beta-globin locus from at least 16 kb 5' to the epsilon gene down to the beta globin gene, along with about 130 kb of flanking DNA. It is thus disclosed here, for the first time, that it is possible to isolate clones from a human r-DNA YAC, library by homologous-recombination selection.

EXAMPLE II

SELECTION BY HOMOLOGOUS-RECOMBINATION OF A r-DNA CLONE FROM A r-DNA YAC LIBRARY USING ONE-STEP GENE DISRUPTION

The method of one-step gene disruption (Rothstein, R. J. Methods in Enzymology, Vol. 101, pp 202–211, Academic Press, New York, 1983) can be adapted for use in the selection of clones from, r-DNA libraries by homologous recombination. In this embodiment of the basic concept, a selectable marker is inserted into the targeting sequence. The targeting sequence, with the embedded selectable marker, is subsequently isolated as a single linear fragment (as diagrammed in FIG. 5) and transformed into the pooled r-DNA YAC library as described in EXAMPLE I. Correctly targeted clones arising as a result of homologous recombination between the targeting molecule and specific r-DNA clones within the library will carry a single copy of the targeting sequence that is disrupted by the presence of the selectable marker. This is in contrast to the process described in EXAMPLE I, in which the correctly targeted r-DNA clones have two uninterrupted copies of the targeting sequence flanking the selectable marker.

FIG. 5 illustrates the selection by homologous recombination of an r-DNA clone from an r-DNA YAC library using one-step gene disruption. The thin line represents an insert of r-DNA in the form of a yeast artificial chromosome (YAC). The solid box is the target sequence, a sequence of r-DNA constituting a portion cof an r-DNA YAC clone found in the library that is homologous to the targeting sequence. In the diagram, the targeting sequence (black boxes) has been modified by the insertion of the yeast ARG4 gene (open box). The remaining portions of the r-DNA YAC are comprised of the YAC vector arms; the thick lines represent plasmid sequences for replication and selection in bacteria. The shaded boxes represent genetic markers used for selection in yeast (yeast selectable markers URA3 and TRP1). The solid arrowheads and circle represent telomeres (TEL) and a centromere/yeast replication origin (CEN/ARS), respectively. a depicts the targeting molecule aligning with the target sequence on the r-DNA YAC. b depicts the product of homologous recombination between the targeting and target sequences, with the targeting sequence having replaced the target sequence.

As a specific example of this embodiment of the basic concept, the 1.9 kb (HindIII) 5' epsilon-globin fragment (see EXAMPLE I) is subcloned into the HindIII site of pUC18 (ATCC #37253). The resulting plasmid is digested with ApaI, dropping out a 0.26 kb ApaI fragment from the central portion of the 5' epislon-globin insert. The 3' ApaI overhangs are made blunt with T4 DNA polymerase, and the resulting material is ligated to the purified ARG4 2.0 kb HpaI fragment [Beacham, I. R., Gene, 29:271–179, 1984]. The resulting plasmid, with ARG4 disrupting the 5' epsilon-globin sequence, is digested with HindIII and transformed, into the r-DNA YAC library as described in EXAMPLE I. The specific example presented results in the replacement of 0.26 kb of the 5' epsilon-globin DNA with the ARG4 sequence, since ApaI is not unique in the targeting sequence. For enzymes that are unique in the targeting sequence, however, the result will be a simple insertion.

EXAMPLE III

HOMOLOGOUS-RECOMBINATION CHROMOSOME WALKING UTILIZING TWO YAC LIBRARIES

A. Construction of Yeast Artificial Chromosome (YAC) Libraries

A.1) *Saccharomyces Cerevisiae* Host Strain Construction

The construction of a strain of *S. cerevisiae* carrying chromosomal deletions of each of the four genes used as selectable markers on the four YAC vectors described can be carried out as follows.

A.1.a) Deletion of ARG4:

The internal 2.0 kb HpaI fragment carrying the entire structural gene and regulatory elements for the yeast argininosuccinate lyase gene (ARG4) is deleted from a plasmid consisting of the 11 kb BamHI fragment isolated from p(SPO13)2 (Wang, H-T., et al., Molecular and Cellular Biology, 7: 1425–1435, 1987) inserted into the BamHI site of pUC19 (ATCC #37254), by digestion with HpaI and religation of the DNA under dilute conditions (1 µg/ml). The resulting plasmid is digested with BamHI and introduced into an *S. cerevisiae* strain carrying the wild-type alleles for ARG4, TRP1, URA3, and LEU2, and carrying any non-reverting his3⁻ allele. The transformation is carried out in conjunction with any plasmid carrying yeast CEN and ARS elements, and the yeast HIS3 gene, using standard co-transformation conditions (Ausubel et al., 1989 Chapter 13). A useful plasmid for this purpose can readily be constructed by subcloning the 1.7 kb BamHI fragment from pRB15 (ATCC #37062) into the BamHI site of YCp50 (ATCC #37419). His⁺ Cells are screened for arginine auxotrophy by replica plating onto CM -arginine plates. His⁺ arg⁻ cells are grown in the absence of selection for HIS3, and single colonies are isolated and screened for histidine auxotrophs. DNA from his⁻ arg⁻ colonies is prepared and analyzed by restriction enzyme and Southern blot analysis to identify transformants carrying the ARG4 deletion (arg4Δ). This protocol is used to generate strain MGD131-10c used in Example I above.

A.1.b) Deletion of TRP1:

In a yeast strain of opposite mating type as that used above, and also carrying mutant alleles for LEU2 and URA3 (leu2-,ura2-), an identical procedure is carried out, but using a linear fragment of DNA carrying a deletion of the yeast gene for N-(5'-phosphoribosyl)-anthranilate isomerase (TRP1). This is accomplished by subcloning the BamHI-XhoI fragment from pBR322-Sc4120 (Stinchcomb, D. T., et al., Journal of Molecular Biology 158:157–179, 1982) into BamHI-XhoI cut pGEM7, (Promega, Madison, Wis.) followed by deletion of the 1.2 kb EcoRI fragment containing TRP1 and ARS1. The resulting plasmid, pK2, is digested with BamHI and XhoI and co-transformed with a HIS3-CEN-ARS plasmid, like that described in A.1.a) above, selecting for histidine prototrophs, and following the strategy outlined in A.1.a) above to identify cells carrying the TRP1 deletion (trp1Δ). These cells are mated with cells carrying arg4Δ, and diploids heterozygous for the two deletions are isolated. This strain, TD7-16d, is sporulated, subjected to tetrad analysis, and spores with appropriate genotypes are analyzed by restriction enzyme and Southern blot analysis to identify a strain with both the arg4Δ and trp1Δ alleles (IV-16d used in Example I above.)

The genotype of TD7-16D is: a/α, arg4Δ/ARG4, LEU2/leu2-3,112, ura3-52/URA3, trp1-289/trp1Δ, ade2-101/ade2-101, cyh$^s$/cyh$^r$, (CYH2/cyh2), his3Δ1/hisΔ1

A.1.c) Deletion of LEU2 and URA3:

Strain TD7-16d is used as the recipient in additional co-transformation experiments, first with a linear DNA fragment carrying an internal deletion of the 1.3 kb HincII-AccI fragment corresponding to the yeast β-isopropylmalate dehydrogenase gene (LEU2), and subsequently with a linear fragment carrying an internal deletion of the 0.85 kb PstI-NsiI fragment corresponding to the yeast orotidine-5'-phosphate decarboxylase gene (URA3). The plasmids YEpl3 (ATCC #37115; (Broach, J. R., et al., Gene, 8:121, 19799) and YIp30 (ATCC #37109; Bothstein, D., et al. Gene, 8:17–24, 1979) are used as sources for constructing deletion derivatives of the LEU2 and URA3 genes, respectively. A diploid that is heterozygous for all four deletions is sporulated, subject to tetrad analysis, and screened for haploid colonies that have the minimal genotype MATa arg4Δtrp1 Δ leu2Δ ura3Δ. This is the recipient strain for constructing Libraries 1 and 2.

A.2. Construction of Yeast Artificial Chromosome (YAC) Vectors

The construction of an artificial chromosome requires that sequences capable of stabilizing the ends of linear DNA, molecules (telomeres or TEL elements) be ligated to each end of the DNA chosen for cloning. In addition, each end needs to carry: 1) a yeast gene that can be used for genetic selection in the initial construction of the library and for use in isolating clone ends for use in selecting clones out of a library by homologous recombination, and 2) a gene that, encodes a protein conferring antibiotic resistance to *E. coli* (selectable markers). Each end should also carry a sequence that functions as an initiation site for DNA replication (an ARS element). Finally, one and only one, of the two ends must carry a sequence that functions as a centromere in yeast (a CEN element).

To ensure that each linear DNA molecule transformed into yeast has two different ends (only one of which carries a CEN element), to facilitate the identification of recovery of each end uniquely, and to generate the two YAC libraries (Library 1 and Library 2), a total of four different ends are needed, utilizing four different yeast genes and four different antibiotic resistance markers. All of the various elements described above are ligated together in specific arrangements to generate yeast artificial chromosome vectors which can be propagated and manipulated in *E.coli*. To minimize the possibility of homologous recombination between the ends of artificial chromosomes in Library 2 and targeting plasmids isolated from Library 1, the bacterial origins of replication on the vectors used in the construction of each individual library are from different sources. So that the final vectors are compact, easy to manipulate, and unlikely to rearrange by virtue of the duplicated bacterial origins of replication, each of the four ends is maintained, as a different plasmid in bacteria, in contrast to the invention described in U.S. Pat. No. 4,889,806.

A.2.a) Construction of a CEN-ARS Element

The PstI site of pUC19 (ATCC #37254) is removed by blunting with T4 DNA polymerase and recircularization with T4 DNA ligase. The resulting plasmid (pUC19/Pst⁻) is cut with EcoRI and SmAI and the 3.1 kb EcoRI-SmaI fragment from A75p9 (carries ARS1, TRP1, and CEN3; Murray, A. W. and Szostak, J. W., Nature, 305:189–193, 1983) is inserted. The resulting plasmid (pT10H) is cut with StuI and BamHI, removing the TRP1 gene and all CEN3 sequences. The StuI-BamII fragment carrying the pUC19/Pst⁻ backbone and ARS1 is gel purified and ligated to a 382 bp Sau3A-ScaI fragment carrying CEN3 isolated from A75p9 (Murray, A. W. and Szostak, J. W., Nature, 305:189–193, 1983). The resulting plasmid (pT12H) carries ARS1 sequences from positions 829–1453 in the published TRP1 sequence (Tschumper, G. and Carbon, J. Gene, 10:157–166, 1980) fused to CEN3 sequences 1–382 (Bloom, K. S. and Carbon, J., Cell, 29:305–317, 1982), with both fragments inserted between the EcoRI and BaHI sites of the pUC19/Pst⁻ polylinker.

A.2.b) Construction of YAC ARM VECTOR pTK-ENDA2

Figure 7A:
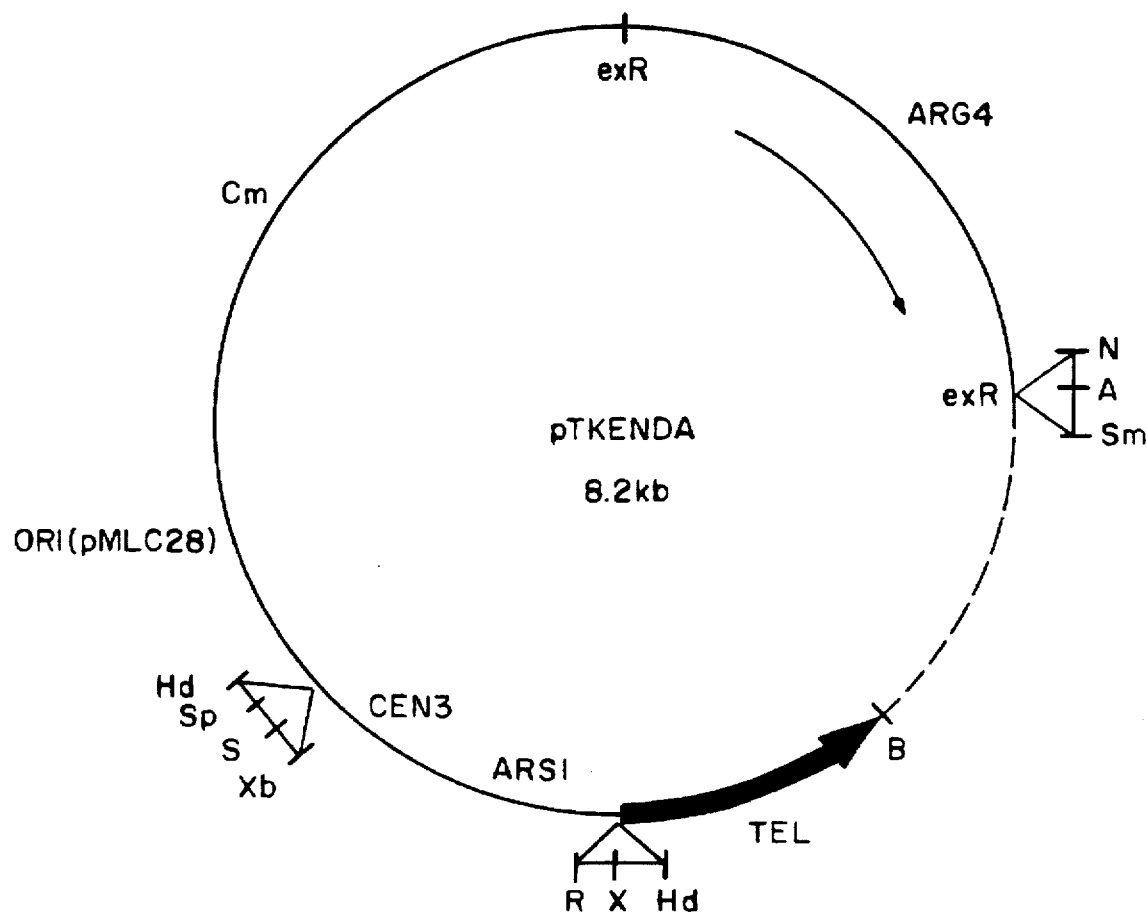
FIG. 7a is a plasmid map of pTKENDA.

The Sau96 site of pMLC28 (pSDC12 with pUC19 polylinker; Levinson, A., et al. Journal of Molecular and Applied Genetics, 2:507–517, 1984) is removed by blunting with T4 DNA polymerase and recircularization with T4 DNA ligase. The resulting plasmid (pMLC28/Sau ) is digested with EcoRI and BamHI, and annealed with oligonucleotides 1 and 2 (FIG. 6a), and treated sequentially with T4 DNA ligase, T4 DNA polymerase, and T4 DNA ligase. The treated molecules are transformed into *E.coli*, and chloramphenicol resistant transformants are screened for the presence of an ApaI site expected to be found in recombinant plasmids carrying the oligonucleotides. Plasmids which also regenerate the EcoRI and BamHI sites are subjected to dideoxy DNA sequence analysis. One plasmid with the correct sequence (pMLC28/SL) is digested with EcoRI, blunted with T4 DNA polymerase, and ligated to the 2.0 kb HpaI fragment carrying the yeast ARG4 gene. (Beacham, I. R., et al., Gene, 29:271–279, 1984). The resulting plasmid with a single insert of the HpaI fragment (pT20) is cut with BamHI and HindIII, and mixed with a purified 0.7 kb BamHI-EcoRI TEL fragment and the 1.0 kb EcoRI-HindIII fragment containing ARS1 and CEN3 from pT12H (Section A.2.a). Transformants resulting from this three way ligation are screened by restriction enzyme analysis. The correct plasmid (pT21) is digested with SmaI and BamHI, and ligated to the 1.8 kb SmaI-BamHI fragment lying at positions 39,890–41,732 on the bacteriophage Lambda map (Lambda DNA available from New England Biolabs, Beverly, Mass.). The resulting plasmid is named pTKENDA. FIG. 7a illustrates the pasmid map of pTKENDA, with relevant features and restriction sites. N: NsiI; A: ApaI; Sm: SmaI; B: BamHI; Hd: HindIII; X: XhoI; R: EcoRI; Xb: XbaI; S: SalI (HincII); Sp: SphI; ARG4: yeast ARG4 gene; Cm: chloramphenicol resistance gene; ORI(pMLC28): pMLC28 origin of replication; CEN3, ARS1: yeast CEN3 (centromere) and ARS1 (replication origin), respectively; TEL: sequence that seeds telomere formation in yeast; exR: former EcoRI sites; dashed line: stuffer DNA fragment derived from bacteriophage Lambda. The arrow indicates the direction of ARG4 transcription.

The CEN3-ARS1 element used in pTKENDA and PTK-ENDD (A.2.e below) is not the preferred sequence to use for constructing r-DNA YAC libraries. To convert pTKENDA to the more preferred derivative, pTK-ENDA is digested with XbaI and treated with the Klenow fragment of *E.coli* DNA polymerase to create a blunt end. This DNA is then cut with BamHI, dropping out the CEN3-ARS1 element originally derived from pT12H (section A.2.a) and the TEL sequence. The 6.5 kb fragment (referred to as fragment A in this modification) carrying ARG4, the lambda DNA stuffer fragment and the chloramphenicol resistance gene is gel purified. Separately, pTKENDA is digested with HindIII and BamHI and the 0.7 kb TEL fragment (referred to as fragment B in this modification) is gel purified.

Plasmid YCp19 (ATCC #37364) is digested with HindIII, PvuII, and XbaI and the 2.6 kb HindIII-PvuII fragment carrying CEN4 and ARS1 is gel purified (referred to as fragment C in this modification). Fragments A, B, and C are ligated together, transformed into *E.coli*, and chloramphenicol resistant colonies are screened for plasmids with a single copy each of fragments A, B, and C. The resulting plasmid is pTK-ENDA2.

A.2.c) Construction of YAC ARM VECTOR pTK-ENDB

The 827 bp EcoRI-PstI fragment from YRp7 (ATCC #37060), carrying the yeast TRP1 gene, is blunted with T4 DNA polymerase and ligated to HincII cut pUC19 (ATCC #37254). One plasmid, pT32H, is isolated in which the direction of transcription of the TRP1 gene is leading away from the EcoRI site of the pUC19 polylinker. This plasmid is cut with EcoRI and BamHI, and annealed with Oligos 3 and 4 (FIG. 6a), and treated sequentially with T4 DNA ligase, T4 DNA polymerase, and T4 DNA ligase. The treated molecules are transformed into *E. coli*, and ampicillin resistant transformants are screened for the presence of an ApaI site expected to be found in recombinant plasmids carrying the oligonucleotides. Plasmids which also regenerate the EcoRI site are subjected to dideoxy DNA sequence analysis. One plasmid with the correct sequence (pT32LH) is purified for further use.

Figure 7B:
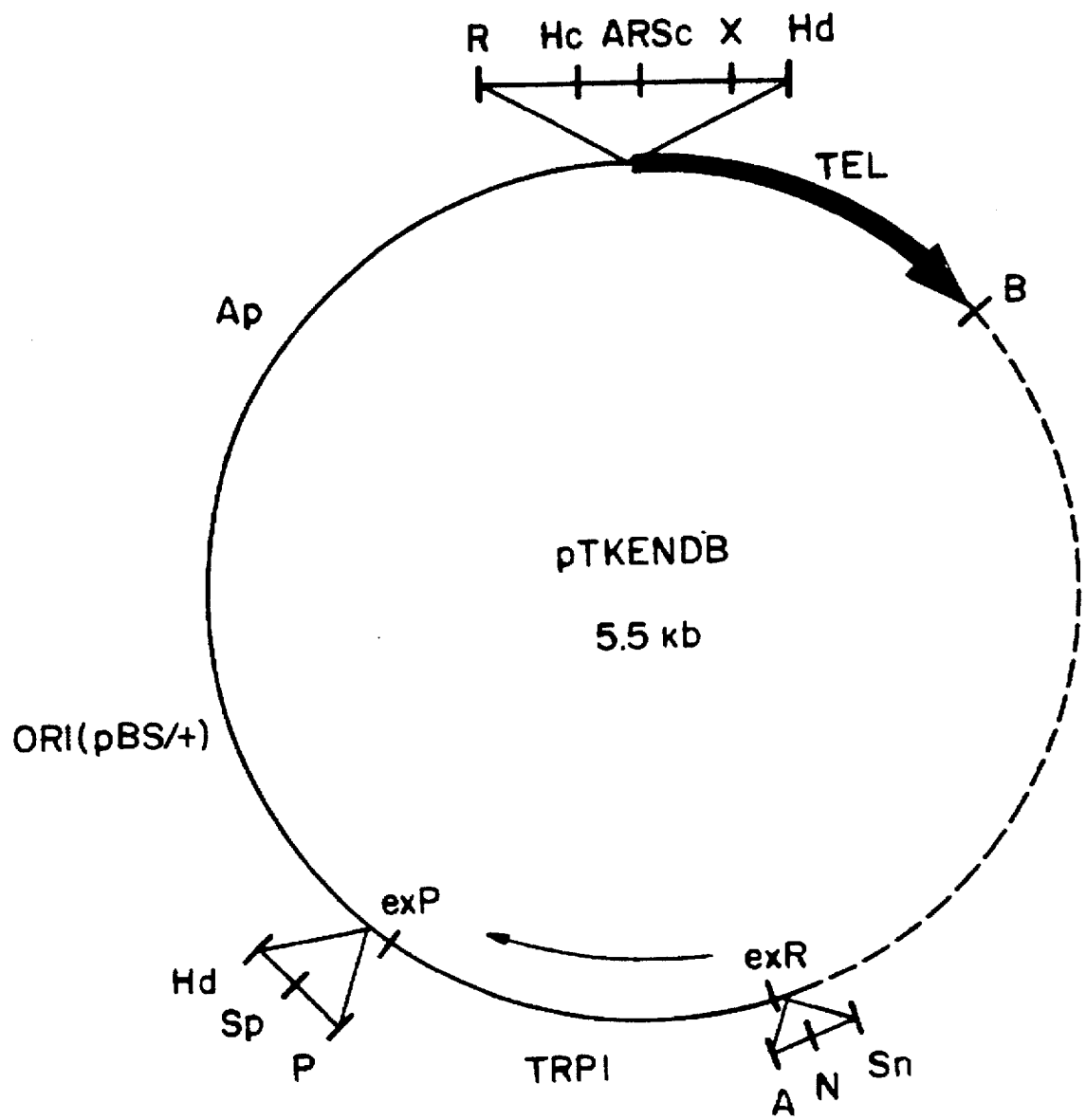
FIG. 7b is a plasmid map of PTKENDB.

Plasmid pBS/+ (Stratagene Cloning Systems, LaJolla, Calif.) is cut with AatII and EcoRI and blunted with T4 DNA polymerase to delete the LacZ gene. The resulting molecules are circularized with T4 DNA ligase and ampicillin-resistant E.coli transformants are analyzed for the correct deletion derivative which regenerates the EcoRI site. One plasmid (PBSA) is cut with EcoRI and PstI (both of which cut within the pBS/+ polylinker), and ligated to the 0.85 kb TRP1 EcoRI-PstI fragment from pT32LH. Ampicillin-resistant transformants from this ligation are screened by restriction enzyme analysis for molecules with the correct structure (pT32BH). pT32BH is then cut with BamHI and XhoI and ligated to the 0.7 kb BamNI-XhoI TEL fragment from pTKENDA, and transformants are screened by restriction (Section A.2.b) enzyme analysis for molecules with a single insert of the TEL fragment. This plasmid, pT33H, is cut with SphI, blunted by treatment with T4 DNA polymerase and recircularized with T4 DNA ligase. The resulting plasmid is pT34H. pT34H is digested with SnaBI and BamHI, and ligated to the 1.2 kb SnaBI-BamHI fragment from plasmid pBR:βa (ATCC #39698). The resulting plasmid is designated pTKENDB. FIG. 7b is a plasmid map of pTKENDB, with relevant features and restriction enzyme recognition sites: N: NsiI; A: ApaI; Sn: SnaBI; B: BamHI; Hd: HindIII; X: XhoI; R: EcoRI; Xb: XbaI; Hc: HincII; Sp: SphI; P: PstI; TRP1: yeast TRP1 gene; Ap: ampicillin resistance gene; ORI(pBS/+): pBS/+ origin of replication; ARSc: consensus ARS sequence (TAAACATAAAA; Broach, J. et al., (1983) Cold Spring Harbor Symp. Quant. Biol. 47:1165). TEL: sequence that seeds telomere formation in yeast; exR, former EcoRI site; exP: former PstI site; dashed line: stuffer DNA fragment derived from human beta-globin DNA. The arrow indicates the direction of TRP1 transcription.

A.2.d) Construction of YAC ARM VECTOR pTK-ENDC

The 622 bp SalI-HindIII fragment from pACYC184 (ATCC #37033; (Chang, A. C. Y. and Cohen, S. N. Journal of Bateriology, 134:1141–1156, 1978) is subcloned into SalI-HindIII cut pBS/– (Stratagene Cloning Systems, LaJolla, Calif.) to generate pT40H. The host strain XL1-Blue (Stratagene Cloning Systems, LaJolla, Calif.) is infected with wild-type M13 (Bio-Rad Laboratories, Rockville Centre, N.Y.) and a mixture of wild-type and pT40H phage particles are isolated. Cells from the dut⁻ung⁻ E.coli strain CJ236 (Bio-Rad Laboratories, Rockville Centre, N.Y.) are infected with this mixture of phage, and a mixture of pT40H and M13 single-stranded DNA is isolated. Oligo 13 (FIG. 6c) is used essentially as described by Kunkel (Kunkel, T. A. Proceedings of the National Academy of Sciences (USA), 82:488–492, 1985) to introduce a C to T substitution at the XhoII site corresponding to position 1870 of pACYC184, to generate pT40/X⁻H. The 622 bp SalI-HindIII fragment from pT40/X⁻H is isolated and ligated to the 3.6 kb SalI-HindIII fragment of pACYC184 purified by gel electrophoresis. The resulting plasmid (pT41H) is cut with XmnI and StyI, blunted by treatment with T4 DNA polymerase, ligated to EcoRI linkers (CGGAATTCCG), and cut with EcoRI to generate EcoRI overhanging ends. The 2237 bp EcoRI-linked XmnI-StyI fragment is purified by gel electrophoresis.

BamHI linkers are added on to the 1.1 kb HindIII fragment from YIp30 (ATCC #37109) that carries the URA3 gene. This fragment is inserted into the BamHNI site of pBS/+ (Stratagene Cloning Systems, LaJolla, Calif.), such that the orientation of URA3 transcription is away from the EcoRI site in the polylinker. The resulting plasmid is cut with HindIII, blunted with T4 DNA polymerase, and recircularized with T4 DNA ligase to remove the HindIII site of the polylinker. The resulting plasmid is cut with NsiI and SalI, blunted with T4 DNA polymerase, and recircularized with T4 DNA ligase to remove the NsiI, BamHI (3' side of URA3 only), XbaI, and SalI sites in the plasmid. The resulting plasmid, is cut with EcoRI and BamHI, and annealed with Oligos 5 and 6 shown in FIG. 6b. The mixture is treated with T4 DNA ligase, T4 DNA polymerase, and again with T4 DNA ligase, and transformed into bacteria. Ampicillin-resistant transformants are screened by restriction enzyme analysis for the presence of an ApaI site introduced with the polylinker, and plasmids that regenerate an EcoRI site are subject to dideoxy DNA sequencing to confirm the correct polylinker sequence. This plasmid is pURA3LH.

Figure 7C:
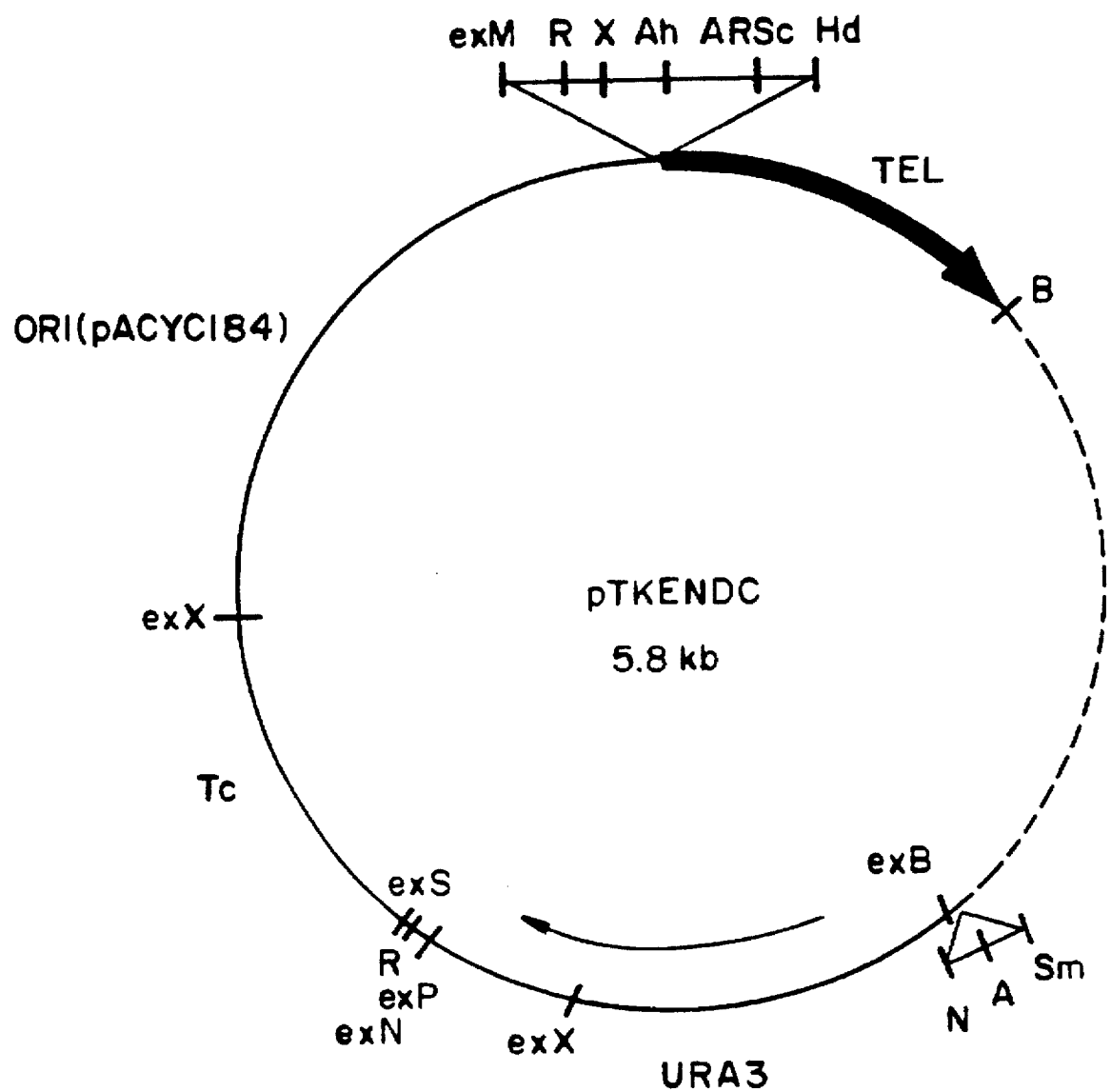
FIG. 7c is a plasmid map of pTKENDC.

The host strain XL1-Blue (Stratagene Cloning Systems, LaJolla, Calif.) is infected with wild-type M13 (Bio-Rad Laboratories, Rockville Centre, N.Y.) and a mixture of wild-type and pURA3LH phage particles is isolated. Cells from the dut⁻ung⁻ E.coli strain CJ236 (Bio-Rad Laboratories, Rockville Centre, N.Y.) are infected with this mixture of phage, and a mixture of pURA3LH and M13 single-stranded DNA is isolated. Oligonucleotide 12 (FIG. 6c) is used essentially as described by Kunkel (Kunkel, T. A., Proceedings of the National Academy of Sciences (USA), 82:488–492, 1985) to introduce a base substitution at the XhoII site at position 906 in the published URA3 sequence (Rose, M., Grisafi, et al., Gene 29:113–114). The resulting plasmid, pURA3LHX⁻ is cut with EcoRI and BamHI and ligated to the 0.7 kb EcoRI-BamHI TEL fragment from pTKENDA (Section A.2.b). The resulting plasmid, pT42H, is cut to completion with EcoRI and partially with PstI, blunted with T4 DNA polymerase, ligated to EcoRI linkers (CGGAATTCCG), and cut with EcoRI to generate EcoRI overhanging ends. The 1.7 kb EcoRI-linked fragment is purified by gel electrophoresis and ligated to the EcoRI-linked fragment from pT41H. Tetracycline resistant transformants are analyzed by restriction enzyme analysis for molecules with a single copy of each fragment in either orientation. This plasmid is digested with BamHI and SmaI and the same 1.8 kb stuffer fragment from bacteriophage Lambda used in the construction of PTK-ENDA is inserted. The resulting plasmid is designated pTKENDC. FIG. 7c is a plasmid map of pTKENDC, with relevant features and restriction enzyme recognition sites. N: NsiI; A: ApaI; Sm: SmaI; B: BamHI; Hd: HindIII; X: XhoII; R: EcoRI; Ah: AhaIII; URA3: yeast URA3 gene; Tc: tetracycline resistance gene; ORI(pACYC184): PACYC184 origin of replication; ARSc: consensus ARS sequence (TAAACATAAAA; Broach, J. et al., (1983) Cold Spring Harbor Symp. Quant. Biol. 47:1165). TEL: sequence that seeds telomere formation in yeast; exS, exM, exN, exP, exB, exX: former StyI, XmnI, NsiI, PstI, BamHII, and XhoII sites, respectively; dashed line: stuffer DNA fragment derived from bacteriophage Lambda. The arrow indicates the direction of URA3 transcription.

A.2.e) Construction of YAC Arm Vector pTKENDD

PACYC177 (ATCC #37031; Chang, A. C. Y. and Cohen, S. N. Journal of Bacteriology, 134:1141–1156, 1978) is cut with Sau96, blunted by treatment with T4 DNA polymerase, and the 1.2 kb fragment carrying the kanamycin resistance gene is isolated by gel electrophoresis. This fragment is ligated to HincII cut pBS/+ (Stratagene Cloning Systems, LaJolla, Calif.) and chloramphenicol and kanamycin resistant clones are analyzed by gel electrophoresis for recombinants with the kanamycin gene inserted such that the direction of transcription is away from the EcoRI site in the pBS/+ polylinker. This plasmid is pT50H. The host strain XL1-Blue (Stratagene Cloning Systems, LaJolla, Calif.) is infected with wild-type M13 (Bio-Rad Laboratories, Rockville Centre, N.Y.) and a mixture of wild-type and pT50H phage particles are isolated. Cells from the dut⁻ung⁻ E. coli strain CJ236 (Bio-Rad Laboratories, Rockville Centre, N.Y.) are infected with this mixture of phage, and a mixture of pT50 H and M13 single-stranded DNA is isolated. Oligonucleotides 14, 15 and 16 (FIG. 6c) are used essentially as described by Kunkel (Kunkel, T. A.,) Proceedings of the National Academy of Sciences (USA), 82:488–492, 1985) to introduce base substitutions at two NsiI sites (positions 2203 and 2469 of the published pACYC177 sequence) and at an XhoII site at position 2602 of pACYC177. The resulting plasmid, pT50HX is cut with EcoRI and SphI, blunted with T4 DNA polymerase, and circularized with T4 DNA ligase, (regenerating the EcoRI site). The resulting DNA preparation is then cut with XbaI. This fragment is ligated to the 882 base pair AccI-XhoII fragment of pACYC177 (which has been blunted with T4 DNA polymerase, ligated with XbaI linkers (GCTCTAGAGC), and treated with XbaI to generate XbaI overhangs) carrying the plasmid origin of replication, to generate plasmid pT51H (either orientation will suffice).

Figure 7D:
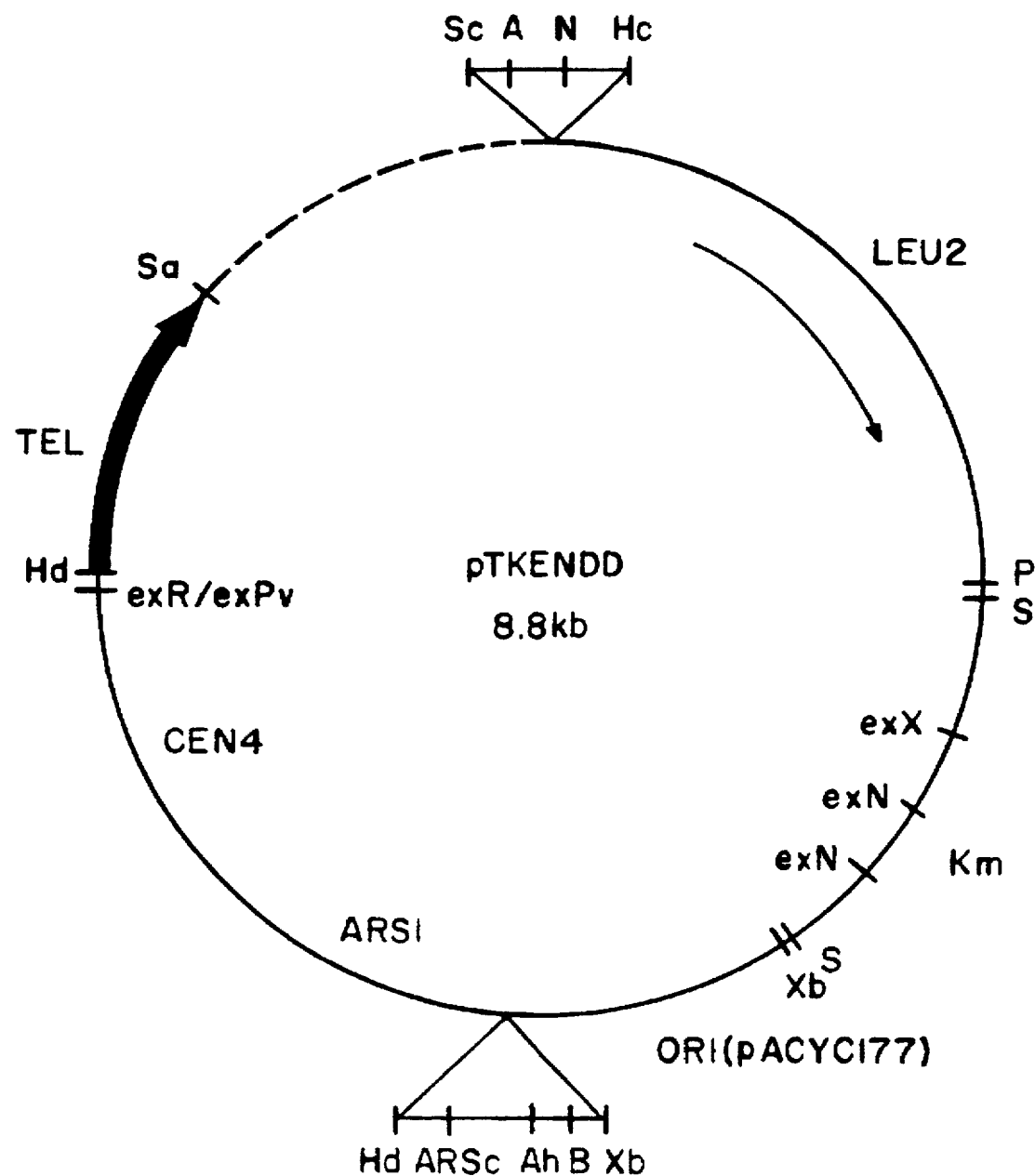
FIG. 7d is a plasmid map of pTKENDD.

Plasmid pT52H is constructed by cutting plasmid YIp33 (ATCC #37064) with HpaI and AccI to release a 1.6 kb fragment containing the yeast LEU2 gene (Andreadis, A., et al., Cell, 31:319–325, 1982). This fragment is blunted with T4 DNA polymerase and ligated to pUC18 (ATCC #37253) cut with HincII. The resulting plasmid is cut with BamHI and XbaI, and annealed with oligonucleotides 7 and 8 (FIG. 6b). The mixture is treated with T4 DNA ligase, T4 DNA polymerase, and again with T4 DNA ligase, and transformed into bacteria. Ampicillin resistant transformants are screened by restriction enzyme analysis for the presence of an ApaI site introduced with the polylinker, and plasmids that regenerate a BamHI site are subject to dideoxy DNA sequencing to confirm the correct polylinker sequence. The resulting plasmid is pT52LH. pT52LH is digested with BamHI and PstI, and the gel purified 1.6 kb fragment is ligated to pT51H cut with BamHI and PstI. The resulting plasmid, pT53H, is digested with ScaI and BglII, and ligated to the double-stranded oligonucleotide shown in FIG. 6c (oligonucleotides 9A and 9B). The resulting plasmid (pT53HL) is digested with BglII and HindIII. Plasmid pTKENDA (SECTION A.2.b AND DEPOSITED) is digested with EcoRI and treated with the Klenow fragment of E.coli DNA polymerase to generate a blunt end. This DNA is then digested with BamHI and the 0.7 kb TEL fragment is gel purified. Plasmid YCp19 (ATCC #37364) is digested with HindIII, PvuII, and XbaI and the 2.6 kb HindIII-PvuII fragment carrying CEN4 and ARS1 is gel purified. The purified CEN4-ARS1 and TEL fragments are ligated to BglII-HindIII digested pT53HL and transformed into E.coli. Kanamycin resistant transformants are screened for plasmids with a single copy each of the CEN4-ARS1, TEL, and pT53HL fragments. The resulting plasmid is pT54H. pT54H is digested with ScaI and SacI, and ligated to the 1.4 kb SacI-ScaI fragment lying between positions 25,881–27,265 on the bacteriophage Lambda (New England Biolabs, Beverly, Mass.) map. The resulting plasmid is pTKENDD. FIG. 7d is a plasmid map of pTKENDD with relevant features and restriction enzyme recognition sites. N: NsiI; A: ApaI; Sc ScaI; ScaI; B: BamI; Hc: HincII; P: PstI, S. SalI(HincII); Hd: HindIII; X: XhoII; Xb: XbaI; Sa: SacI; Ah: AhaIII; LEU2: yeast LUE2 gene; Km: Kanamycin resistance gene; ORI (pACYC177): pACYC177 origin of replication; ARSc: consensus ARS sequence (TAAACATAAAA; Broach, J. et al., (1983) Cold Spring Harbor Symp. Quant. Biol. 47:1165). CEN4/ARS1: CEN4/ARS1 fragment from YCp19 (see text); TEL: sequence that seeds telomere formation in yeast; exR, exPv, exN, exX: former EcoRI, PvuII, NsiI and XhoII sites, respectively; dashed line: stuffer DNA fragment derived from bacteriophage Lambda. The arrow indicates the direction of LEU2 transcription.

A.3.) Construction of Yeast Artificial Chromosome (YAC) Libraries

A.3.a) Preparation of High Molecular Weight DNA and Ligation of High Molecular Weight DNA to YAC Vector Arms DNA from human white blood cells is prepared and partially digested with restriction endonucleases, essentially as described (D. Burke, Ph.D. Thesis, Washington Univ., St. Louis, Mo. (1988)). DNA (with a desired average size of greater than 1.5 megabases) is partially digested with ApaI, NsiI, or any enzyme that leaves a blunt end. To construct Library 1, plasmids pTKENDA2 and pTKENDB are used. pTKENDA2 is cleaved with BamHII and either ApaI, NsiI, or SmaI to release the stuffer fragment. pTKENDB is cleaved with BamHI and either ApaI, NsiI, or SnaBI to release the stuffer fragment. For the construction of Library 2, plasmids pTKENDC and PTKENDD are used. pTKENDC is digested with BamHI and either ApaI, NsiI, or SmaI to release the stuffer fragment. pTKENDD is digested with SacI and either ApaI, NsiI, or ScaI to release the stuffer fragment.

Each vector is treated with calf intestine alkaline phosphatase under conditions recommended by the supplier and purified by phenol extraction and ethanol precipitation. For each library, 50 μg of human DNA and 25 μg of each vector in each pair pTKENDA2 pTKENDB or pTKENDC-pTKENDD) are mixed and ligated using T4 DNA ligase for 2 days at 12° C., in a ligation buffer recommended by the enzyme supplier. The ligated DNA is size fractionated by Field Inversion Gel Electrophoresis (Carle et al., Science, 232; pp 65–68, 1986) in low-gelling temperature agarose (FMC Corp., Rockland, Me.), or CHEF gel electrophoresis (Chu et al., 1986 op cit) and the portion of the gel containing DNA of 250–450 kb is excised and equilibrated with TE buffer+45 mM NaCl.

A.3.b) Transformation of Yeast SpheroPlasts with DNA, Ligated to YAC Vector Arms and Selection of Yeast Cells CarryinQ Artificial Chromosomes DNA prepared as described in section A.3.a can be used to transform a haploid *Saccharomyces cerevisiae* strain carrying chromosomal deletions for ARG4, TRP1, URA3, and LEU2 to arginine and tryptophan prototrophy using human DNA ligated to pTKENDA2 and pTKENDB, essentially as described by Burgers and Percival (1987), with the following modifications: 10–20 μl of the low-melt agarose carrying the DNA is melted at 68° C. for 3 to 5 minutes. Carrier DNA (sheared salmon sperm or calf thymus DNA) is added to the cells to a final concentration of 30–40 μg/ml immediately before 200 μl of cells is added to the melted gel slice.

For plating and selection of yeast cells carrying artificial chromosomes, transformed cells are mixed with top agar (1M sorbitol, 2% dextrose, 0.5% ammonium sulfate, 0.17% yeast nitrogen base (Difco), 2.5% Bacto-agar (Difco), 0.005% adenine sulfate, and supplemented with uracil and all of the amino acids listed in Table 13.1.1 of Ausubel et al. (Ausubel et al., 1989) at the listed concentrations, but omitting arginine and tryptophan for selection. The mixture of cells and top agar is poured onto the surface of agar plates made identically to the top agar except that the final concentration of agar is 2% in the plates. Plates are incubated at 30° C. for 5–7 days.

To construct Library 2, human DNA ligated to pTKENDC and pTKENDD are used to transform the same *S. cerevisiae* strain to uracil and leucine prototropy. Top agar and plates are prepared as described above, but lacking only uracil and leucine.

A.3.c) Pooling of Clones

Yeast colonies growing on plates selective for markers present on artificial chromosomes are transferred using sterile toothpicks into individual wells of 96-well microtiter plates filled with 200 μl of selective media. Plates are incubated with shaking at room temperature for 2 days and stored at 4° C. for up to one week. A fully representative YAC library of the human genome should be comprised of 50,000 independent clones., assuming an average clone size of 300 kb. This number of clones would fill 521 microtiter plates and is stored as 10 separate subpools. When approximately 52 plates are filled, 100 μl from each well is withdrawn, pooled, and thoroughly mixed with an equal volume (approximately 500 ml) of 30% sterile glycerol. The cell density of the cells in glycerol should be about $2.5 \times 10^7$ cells/ml, and can be adjusted to this density by counting cells prior to glycerol addition. The pooled cells are then aliquoted into microcentrifuge tubes in volumes of 0.1 to 1 ml. This is repeated for each of the 10 separate subpools.

B.) Transformation of Pooled Library 1 with a Targeting Plasmid and Selection of Specific Artificial Chromosome Clones The isolation of r-DNA YACs by homologous recombination is illustrated in Steps 1 and 2 of FIG. 8.

B.1.) Construction of the Targeting Plasmid

The desired fragments of human DNA (the targeting sequences), previously identified as being unique in the human genome are substituted for the TEL and stuffer domains of pTKENDC. 50 μg of the resulting subclones are prepared and digested to completion with a restriction endonuclease which generates a linear molecule harboring a double-strand break or gap in the targeting sequence, in such a manner that at least 150 base pairs of targeting DNA remains on either side of the break or gap, and the pTKENDC vector backbone is intact and contiguous with the targeting DNA. The digested DNA is purified by phenol extraction and ethanol precipitation and resuspended in 20 μl.

B.2.) Transformation of YAC Library 1 with the Targeting Plasmid and Selection of Clones Homogolous to the Targeting Sequence 0.1 ml of each of the 10 subpools are combined in 10 100 ml CM -arg, trp selective media supplemented to 0.05× YPD. Cells are grown overnight with vigorous shaking at 30° C. to a density of $2 \times 10^7$ cells/ml. Cells are prepared for transformation by the lithium acetate method (Ito et al., 1983) essentially as described (Ausubel et al., Chapter 13, 1989), and split into six 200 μl aliquots at $2 \times 10^9$ cells/ml. 50 μg of each of the linearized targeting plasmids (in 20 μl) is mixed with 10 μg (2 μl) sonicated calf thymus DNA and added to a 200 μl aliquot of cells. After transformation, cells are spread onto the surface of CM—arginine, tryptophan, and uracil agar plates and incubated at 30° C. for 3–5 days. The omission of uracil from the media selects for cells that have stably integrated the targeting plasmid derived from pTKENDC.

C.) Analysis of Clones

C.1.) Segregation Analysis of Clones

Yeast colonies prototrophic for arginine, tryptophan, and uracil are candidates for clones carrying the targeting plasmid integrated into a human r-DNA YAC with a region of identity to the targeting sequences on the targeting plasmid. Colonies in which the targeting plasmid integrated into a YAC are identified by a marker segregation assay. The loss patterns of the three markers are analyzed in cells derived from the selected clone which have lost the YAC after growth on non-selective media. Cells are patched onto YPD plates and grown non-selectively for two days, replica printed onto a second YPD plate and grown for another two days. Cells from the second YPD plate are struck-out for single colonies on a third YPD plates. After three days, the plate with single colonies is replica printed onto a CM -arginine, tryptophan plate, and a CM -uracil plate. Clones in which the targeting plasmid is integrated into a YAC are identified by their characteristic pattern of co-loss of all three markers. In these cases all colonies that are auxotrophic for arginine and tryptophan (colonies that lost the markers identifying the YAC) are also auxotrophic for uracil.

C.2.) Restriction Enzyme and Southern Blot Analysis of Clones

Total DNA is prepared from yeast colonies prototrophic for arginine, tryptophan, and uracil. The DNA is digested with the same restriction enzyme used to generate the double-strand break in the targeting sequence. 1 μg of the digested DNA is subject to agarose gel electrophoresis and Southern transfer and probed with 32-P labeled DNA corresponding to the fragment of the URA3 gene carried in pTKENDC. As a control, 1 ng of the. digested plasmid generated in B.1.) above is run alongside the yeast DNA samples. A correctly targeted event is characterized by a band on the autoradiograph that migrates exactly the same distance as the pure, linearized targeting plasmid.

C.3.) Rescue of Clone Termini to Generate Labeled Probes, Southern Blot Analysis to Identify Seguences that are Single Copy in the Genome Under Analysis, Determination of the Orientation of Cloned Inserts Relative to Vector Arms. Generation of a Targeting Vector from Clone Termini, and Transformation Into Pooled Library 2

The YAC cloning vectors pTKENDA2, pTKENDB, pTKENDC, and pTKENDD have been designed specifically to facilitate the rescue of cloned DNA from the ends of r-DNA YACs by simple microbiological techniques. One or more recognition sites for restriction enzymes that cut mammalian DNA relatively frequently (approximately once every 0.5–1.5 kb) are positioned at the junction between the bacterial plasmid replicon and the yeast telomere (TEL) or yeast replication origin (ARS) and centromere (CEN) sequences. For any one of the four ends, recognition sites for a subset of such enzymes are not found at any other position in the plasmid replicon or the yeast selectable marker on that end, such that cleavage of total yeast DNA isolated from cells carrying a particular r-DNA YAC with one of these enzymes rescues (as illustrated in step 3 of FIG. 8) DNA from the cloned insert covalently linked to the yeast-selectable marker and bacterial replicon, but free of yeast chromosome stability elements (telomeres, centromeres, and yeast replication origins). This "rescued" DNA is used as the targeting plasmid for the second r-DNA YAC library. TABLE 1, COLUMN 2 (RESCUE SITES) lists the restriction enzymes useful for rescuing cloned DNA adjacent to each of the four ends in the two r-DNA YAC libraries. COLUMN 3 (ADDITIONAL ENZYMES) lists some of the additional enzymes that can be used in conjunction with the enzymes listed under RESCUE SITES in the event that a RESCUE SITE enzyme rescues a very long sequence containing a repetitive DNA element that might prevent the clone from being useful for selecting r-DNA YACs by homologous recombination.

| YAC END | RESCUE SITES | | ADDITIONAL ENZYMES | |
|---------|--------------|--------|--------------------|--------|
| pTKENDA2 | HincII | (1433) | PstI | (3169) |
| | HindIII | (1844) | XhoI | (21462) |
| | SphI | (4522) | EcoRI | (2669) |
| | | | BamHI | (5604) |
| | | | KpnI | (8902) |
| | | | StuI | (3872) |
| | | | AvaII | (790) |
| | | | HpaI | (4240) |
| pTKENDB | HincII | (1433) | XhoI | (21462) |
| | EcoRI | (2669) | TthIII1 | (1070) |
| | | | StyI | (785) |
| | | | BamHI | (5604) |
| | | | KpnI | (8902) |
| | | | StuI | (3872) |
| | | | HpaI | (4240) |
| pTKENDC | AhaIII | (1192) | TthIII1 | (1070) |
| | BstYI | (930) | XhoI | (21462) |
| | EcoRI | (2669) | BamHI | (5604) |
| | | | KpnI | (8902) |
| | | | HpaI | (4240) |
| pTKENDD | AhaIII | (1192) | HgiAI | (1348) |
| | BstYI | (930) | HpaI | (4240) |
| | BamHI | (5604) | SphI | (4522) |

The numbers in parentheses represent the average number of base pairs between restriction sites calculated for mammalian DNA.

Figure 8A:
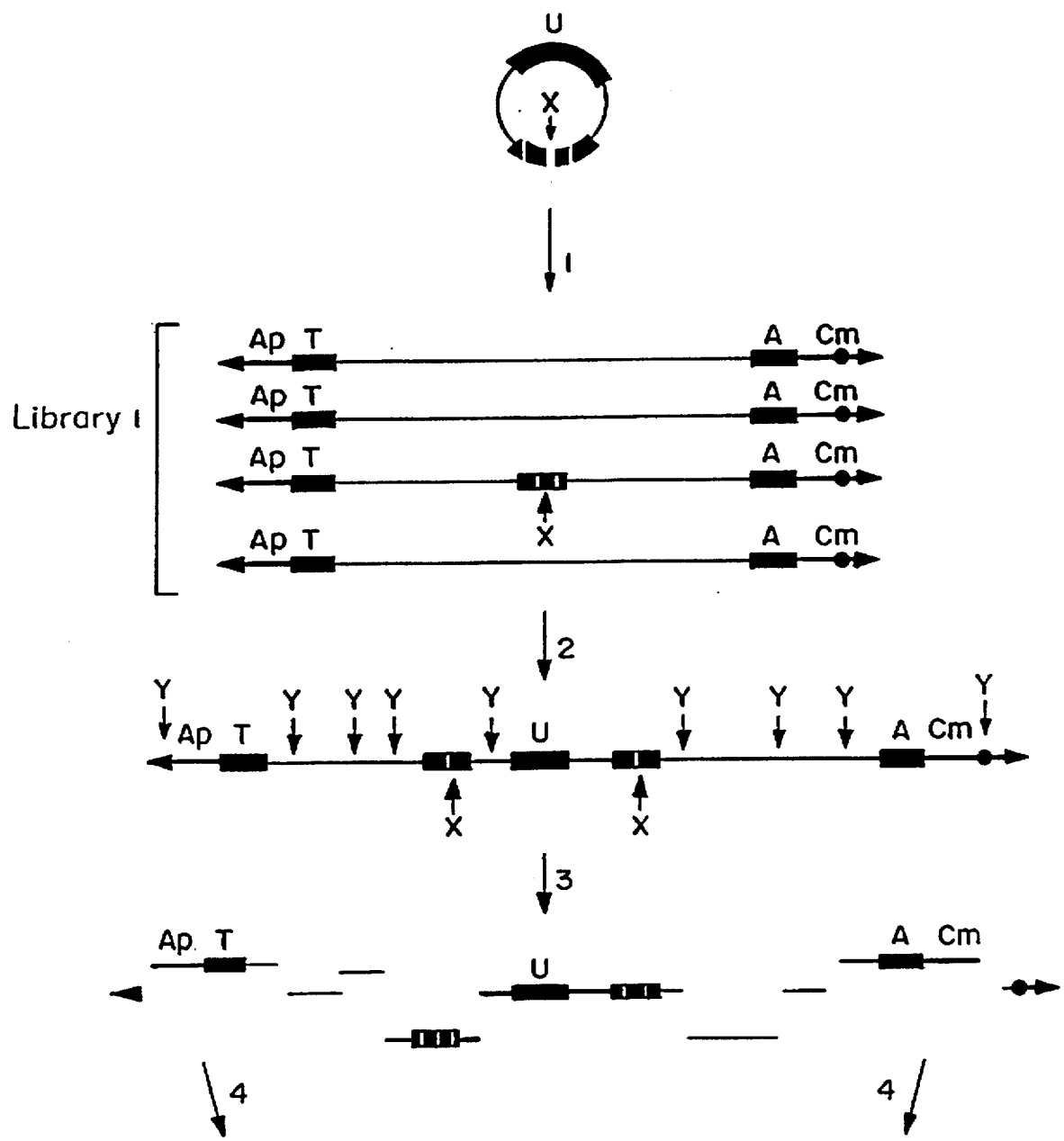
FIG. 8a & 8b illustrates selection of r-DNA clones by homologous recombination using two r-DNA YAC libraries.
Figure 8B:
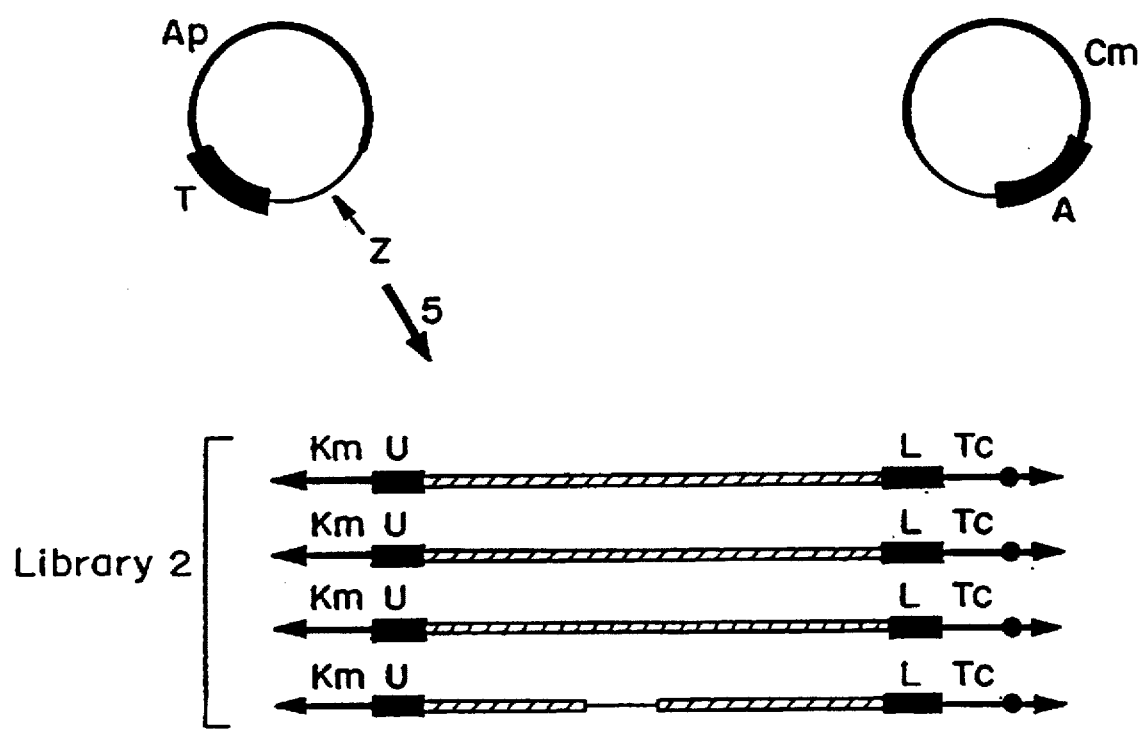

The recovery, analysis, and use of clone termini for recombination walking is illustrated in Steps 3–6 of FIG. 8, selection of r-DNA YAC clones by homologous recombination using two r-DNA YAC libraries. U: yeast URA3 gene; X: restriction enzyme cleavage site used to make targeting break; striped box: targeting sequence; thick lines: plasmid sequences for propagation and selection in *E.coli*; Ap: ampicillin resistance gene; Cm: chloramphenicol resistance gene; T: yeast TRP1 gene; A: yeast ARG4 gene; solid circles and horizontal arrowheads: yeast centromere/replicaticon origins and telomeres, respectively; thin lines: cloned human DNA in Library 1; Y: restriction enzyme cleavage sites used for end-rescue; L: yeast: LEU2 gene; Km: Kanamycin resistance gene; Tc: tetracycline resistance gene; Z: restriction enzymne cleavage site used to make targeting break in end-rescued DNA; thick shaded line: cloned human DNA in Library 2. The thin line in Library 2 DNA represents a sequence homologous to end-rescued DNA from Library 1. The remainder of the discussion will relate to isolating (rescuing) the left-hand end of the YAC, but the principles can be extrapolated for homologous recombination walking using any of the four ends in the two r-DNA Libraries. The vertical arrows marked "Y" can represent the positions of HincII sites lying at various positions throughout the human DNA (for mammalian genomes, HincII sites have an expected distribution of 1 site/1.4 kilobases). The vertical arrow on the extreme left side indicates the position of a HincII site that separates the TEL element from the TRP1-pBSΔ element. Cleavage of total DNA from the yeast strain carrying the YAC illustrated will release the TRP1-pBSΔ fragment from the TEL sequence on the left side, but the right side will remain attached to a fragment of cloned DNA extending to the first HincII site within the insert. The total DNA is ligated under conditions which promote circularization of fragments. A fraction of this DNA is used to transform bacterial cells to isolate ampicillin resistant plasmids.

Approximately 60 μg of plasmid DNA is purified, and several micrograms are digested with HincII and the enzyme used to digest the genomic DNA constituting the library (SnaBI, ApaI, or NsiI). If Library 1 was constructed by cleaving genomic DNA with SmaI and ligated to the SnaBI digested pTKENDB, then an enzyme other than SmaI or SnaBI which flanks the cloning site must be used (for example, ApaI or NsiI). The digest is fractionated on an agarose gel and the non-YAC vector fragment (the rescued insert) is purified and a fraction is labeled with $^{32}$-phosphorus or chromogenic nucleoside triphosphates. This servies three purposes:

1. 1. The DNA is cut with a selection of restriction enzymes that are known not to cut within the TRP1 pBSΔ sequence. (ADDITIONAL ENZYMES in Table I can be used). The digestion products are analyzed by gel electrophoresis to identify restriction enzymes which will cut the cloned DNA isolated from the end of the YAC.
2. The labeled DNA is used to probe a Southern blot filter of human and yeast DNA to determine if the end of the YAC corresponds to a single copy sequence in the human genome, or if it is homologous to the yeast genome. Human sequences that are single copy and not homologous to yeast DNA are preferred for targeting.
3. The labeled DNA is used to probe a dot-blot, in which total DNA from yeast cells carrying YACs has been isolated and fixed to a Nylon membrane. The membrane is spotted with DNA from the YAC that the labeled DNA is amplified from (YAC-Z), the YAC overlapping with YAC-Z which is used to isolate YAC-Z in the previous recombination selection step (YAC-Y), and the YAC overlapping with YAC-Y which was used to isolate YAC-Y in the previous recombination selection step (YAC-X) [i.e., the last three YACs isolated in the walk]. Hybridization only to the YAC from which it is derived (YAC-Z in this case) indicates that the TRP1-pBSΔ end of YAC-Z extends in the correct direction, away from the YACs Y and X. This is confirmed by a similar analysis with the other end of YAC-Z, which must hybridize with YAC-Z and YAC-Y.

A targeting plasmid meeting the criteria outlined in 2) and 3) above is cleaved with an appropriate restriction enzyme (identified from 1 above) and as denoted as Z in FIG. 8), and used as the targeting plasmid to isolate clones from Library 2, as described in Section B.2 above.

EXAMPLE IV

METHODS FOR PREVENTING THE OCCURRENCE OF REPETITIVE INTERSPERSED DNA AS r-DNA CLONE TERMINI

The vectors described in Example III incorporate novel features that are specifically designed to facilitate chromosome walking. First, the two ends of the artificial chromosome are derived from two different plasmids, each with its own sequence to seed telomere formation in yeast, a bacterial origin of replication, a gene for resistance to an antibiotic for selection in E.coli, and a selectable gene for clone selection in yeast. This system allows either end of the YAC to be isolated as a bacterial plasmid for amplification and use in each walking step, as opposed to the possibility of isolating only one end with existing YAC vectors.

In the preferred embodiment of any walking strategy, the extreme end of a clone is used as a probe to isolate overlapping clones in the walk. The usefulness of such a probe is limited by the presence of repetitive DNA which recognizes and hybridizes to thousands of clones within the library. Members of the class of DNA sequences termed highly repetitive interspersed are found at thousands of discreet locations throughout the human genome. Specifically, a member of the Alu family of repetitive DNA sequences is found, on average, spaced at 1 to 3 kilobase interval throughout the genome (Moyzis, R. K., et al., Genomics, 4:273–2889, 1989).

The methods and vectors described in Example III have been designed to minimize the occurrence of repetitive DNA at: the terminus of the r-DNA clone inserts in a human r-DNA YAC vector library. The first feature incorporated into the vector library design is the use of a specific set of restriction endonucleases to cleave human DNA. Numerous DNA sequences from the Alu and L1 family of repetitive DNA were analyzed using computer programs that identify recognition sites for restriction endonucleases. The results of this analysis revealed that recognition sites for the restriction enzymes ApaI, NsiI, and ScaI are not found in the published consensus sequences for any of the Alu subfamilies, and are found only rarely in sequenced members of the L1 family (of approximately 30,000 base pairs of sequenced L1 DNA analyzed, there were only five sites for the three enzymes listed above; 23 sites would be expected based on the dinucleotide frequencies found for human DNA). These two families alone account for approximately 10% of the mass of the human genome, indicating that as many as one in ten clone ends (1 in 5 clones) may terminate within one of these repetitive sequences. By using the enzymes disclosed above to cleave human DNA, one creates an inherent bias against the occurrence of these two repetitive sequences at the ends of clones.

The second feature incorporated into the design of the YAC cloning vectors to minimize the occurrence of repetitive DNA in targeting probes used for walking is limiting the size of the DNA probe fragment rescued from the r-DNA clone end. Smaller DNA fragments have a lower probability of containing repetitive DNA. The vectors described in Example III have been designed to rescue fragments of human DNA on the order of 1 kb in length by a single restriction enzyme cleavage of the YAC clone. This is accomplished by the insertion of a polylinker carrying recognition sites for multiple restriction enzymes which cut, on the average, once every 0.5–1.5 kb. When total DNA from yeast carrying the YAC is cut with one of these enzymes, a fragment of DNA containing a plasmid origin of replication and a drug resistance marker (for propagation and selection in E.coli, as well as a gene for selection in yeast, and approximately 1 kb of human DNA will be released. This fragment can be circularized and transformed into bacteria. As expected, the recognition sites for enzymes that are most useful for this step are found within several of the elements used in the construction of the proposed YAC cloning vectors. In vitro mutagenesis to delete restriction enzyme cleavage sites, along with the judicious choice of combinations for the two plasmid replication origins, the four drug-resistance markers, and the four yeast selectable markers is used to create vectors lacking the frequent-cutting restriction enzyme cleavage sites listed in TABLE I (RESCUE SITES).

The specific materials and methods employed in Examples I–IV are not meant to limit the scope of the claims. One of ordinary skill in the art will know how to make routine substitutions and alterations in the specific exemplary materials and methods disclosed in the embodiments of the Examples, e.g., in the host yeast strains, in the selectable markers, centromeres, telomeres,, autonomously replicating sequences, plasmid origins of replication, drug resistance markers, restriction enzymes, restriction endonuclease recognition sites, oligonucleotide sequences, etc. For example, one of ordinary skill in the art will know how to design alternative oligonucleotide sequences containing recognition sites for restriction endonucleases that are desirable for separating the elements necessary for chromosome replication in yeast away from the r-DNA YAC clone terminus and the elements necessary for replication in bacteria, as described in Example III.

One of ordinary skill in the art will know how to substitute a double-strand gap into a targeting sequence, rather than a simple double-strand break; or how to modify free ends adjacent to, the break or gap to prevent circularization, such modifications including, but not limited to the addition of dideoxyribonucleotides to the 3' ends of the DNA or the use of two different restriction endonucleases to generate non-complementary ends.

The choice of the yeast selectable marker gene can be made from among many and various endogenous yeast gene loci, e.g., ARG4, LEU2, HIS3, HIS4, THR1, URA3, TRP1, LYS2, ADE2, ADE8, MET2, etc. Alternatively, the yeast selectable marker may be a marker gene that is not endogenous to the yeast genome, but is a foreign gene that confers a selectable phenotype, e.g., a bacterial gene that confers drug resistance to yeast cells (such as the CAT or neo genes from transposons Tn9 and Tn903, respectively) or amino acid or nucleoside prototrophy (such as E. coli argH, trpC, or pyrF genes).

The suitable selectable marker genes for selection in bacteria other than the exemplified chloramphenical resistance gene from transposon Tn9 would include genes encoding resistance to the antibiotics, karamycin, ampicillin, tetracycline, spectinomycin, streptomycin, erythromycin, or any other marker, including genes encoding biosynthetic enzymes for which auxotrophic bacterial hosts exist.

Bacterial origins of replication may be derived from a variety of sources, including pACYC184, ColE1, phage M13, phage f1, phage Lambda, or any other replicon that one trained in the art would recognize as providing an equivalent function.

The rescue of r-DNA clone termini described in Example III utilizes restriction endonucleases to cleave a r-DNA clone in such a manner that the terminus is covalently attached to a fragment of the YAC vector arm. One of ordinary skill in the art will know how to isolate r-DNA clone termini by use of various embodiments of the polymerase chain reaction (PCR), with such reaction using a unique primer that anneals to the YAC vector arm immediately adjacent to the r-DNA cloning site, such that the first strand synthesis proceeds away from the YAC vector arm and copies cloned DNA, and in which specific restriction enzyme cleavage sites comprise part of one or both of the PCR primers which would facilitate the subcloning of terminal fragments from r-DNA YACs.

The DNA used to construct the r-DNA libraries may be cDNA or genomic DNA which is derived from human sources or any other organism.

The materials and methods disclosed embody the preferred use of yeast artificial chromosomes as the vectors of choice for a r-DNA library in a yeast host, one of skill in the art could use other known yeast vectors such as YCp vectors, e.g., YCp50 or YCp19, to construct a r-DNA library with which to practice homologous-recombination screening methods and homologous-recombination walking methods disclosed herein. The above is not an inclusive recitation of the alterations and modifications one of skill in the art could make to the specific materials and methods of the inventions embodied in the Examples, and yet remain within the spirit and scope of the inventions as taught and claimed.

What is claimed:

1. A homologous-recombination method for screening a recombinant-DNA (r-DNA) library constructed in host yeast cells and isolating a desired r-DNA clone sequence present as a single copy or in low-copy number in the library, comprising the steps of:
    a) providing a r-DNA library in a population of host yeast cells, wherein the host yeast cells are Saccharomyces or Schizosaccharomyces;
    b) introducing into the population of host yeast cells containing the r-DNA library a targeting DNA molecule which is non-replicating in the yeast host and comprises a selectable marker gene for selection in the host yeast cells and a targeting DNA sequence homologous in part to a target r-DNA clone sequence contained as a single copy or in low-copy number in the r-DNA library;
    c) selecting a host yeast cell containing a target r-DNA clone sequence having stably incorporated therein by homologous recombination the selectable marker gene for selection in the host yeast cell and a portion of the targeting DNA sequence present in the tareting DNA molecule; and
    d) isolating the target r-DNA clone sequence from the host yeast cell selected in step c).

2. The method of claim 1 wherein the targeting DNA molecule is a plasmid.

3. The method of claim 2 wherein the targeting plasmid has a double-strand break introduced within the targeting sequence.

4. The method of claim 1 wherein the targeting DNA molecule is a linear DNA fragment and the targeting DNA sequence is disrupted by the insertion of the selectable marker for the host cell into the targeting sequence.

5. A homologous-recombination method for screening a population of recombinant-DNA (r-DNA) clones present as a yeast artificial chromosome (YAC) library in host yeast cells which are Saccharomyces and isolating a desired r-DNA clone sequence present as a single copy or in low-copy number in the library, comprising the steps of:
    a) providing a r-DNA YAC library in a population of host yeast cells;
    b) introducing into the population of host yeast cells containing a r-DNA YAC library a targeting DNA molecule which is non-replicating in yeast and comprises a selectable marker gene for selection in yeast and a targeting DNA sequence homologous in part to a target r-DNA clone sequence contained in the r-DNA YAC library as a single copy or in low-copy number;
    c) selecting a transformed host yeast cell containing a YAC having the selectable marker gene for selection in yeast and a portion of the targeting DNA sequence stably incorporated therein; and
    d) isolating the YAC from the host yeast cell selected in step c).

6. The method of claim 5 wherein the targeting DNA molecule is a plasmid.

7. The method of claim 6 wherein the targeting plasmid has a double-strand break introduced within the targeting sequence.

8. The method of claim 5 wherein the targeting DNA molecule is a linear DNA fragment and the targeting DNA sequence is disrupted by the insertion of the selectable marker for yeast into the targeting sequence.

9. A method of producing a human recombinant DNA (r-DNA) library, comprising r-DNA clone inserts, wherein there is a bias against the occurrence of Alu and L1 repetitive DNA sequences at the termini of the r-DNA clone inserts, comprising:
    a) digesting human genomic DNA with a restriction endonuclease selected from the group consisting of ApaI, NsiI and ScaI, thereby producing human DNA fragments and selecting against the occurrence of Alu and L1 repetitive DNA sequences at the termini of the product DNA fragments; and
    b) incorporating human DNA fragments produced in a) into YACs, thereby producing a human r-DNA YAC library.

10. A method for isolating contiguous DNA segments, comprising the steps of:
    a) providing a recombinant DNA (r-DNA) library in a population of host yeast cells, wherein the host yeast cells are Saccharomyceo or Schizosaccharomyces;
    b) introducing into the population of host yeast cells containing the r-DNA library a first targeting DNA molecule which is non-replicating in yeast and comprises a selectable marker gene for selection in yeast and a targeting DNA sequence homologous in part to a target r-DNA clone sequence contained in the r-DNA library as a single copy or in low-copy number, under conditions appropriate for viability of the host yeast cells, such that homologous recombination occurs between the targeting DNA sequence and a target r-DNA clone sequence, whereby the selectable marker gene for selection in yeast and a portion of the targeting DNA sequence in the targeting DNA molecule are stably incorporated by homologous recombination into a target r-DNA clone sequence;

c) selecting a host yeast cell containing a target r-DNA clone sequence having stably incorporated therein by homologous recombination the selectable marker gene for selection in yeast and a portion of the targeting DNA sequence present in the targeting DNA molecule;

d) isolating DNA containing the target r-DNA clone sequence from the host yeast cell selected in step c), thereby obtaining a first target r-DNA clone sequence;

e) subcloning a terminus of the first target r-DNA clone sequence into a DNA molecule which is non-replicating in the host yeast cell and contains a selectable marker gene for selection in the host yeast cell, thereby producing a second targeting DNA molecule which is non-replicating in the host yeast cell and includes the selectable marker gene for selection in the host yeast cell and the subcloned terminus of the first target r-DNA clone sequence, wherein the subcloned terminus of the first target r-DNA clone sequence is homologous in part to a second target r-DNA clone sequence contained in the r-DNA library;

f) introducing the second targeting DNA molecule into a population of host yeast cells containing the r-DNA library; and g) selecting a host yeast cell containing a second target r-DNA clone sequence having the selectable marker for selection in the host yeast cell and a portion of the subcloned terminus of the first intact target r-DNA clone sequence stably incorporated therein by homologous recombination, thereby obtaining a second r-DNA clone sequence with a DNA segment contiguous to the subcloned terminus of the first r-DNA clone sequence.

11. The method of claim 10 wherein the first targeting DNA molecule and the second targeting DNA molecule are plasmids.

12. The method of claim 10 wherein the first targeting DNA molecule and the second targeting DNA molecule each have a double-strand break introduced within the targeting sequence.

13. The method of claim 10 wherein the first targeting DNA molecule and the second targeting DNA molecule are linear DNA fragments and the target DNA sequence is disrupted by the insertion of the selectable marker for yeast into the target sequence.

14. The method of claim 10 wherein the second targeting DNA sequence has a double-strand break within the sequence.

15. A method for isolating contiguous DNA segments, comprising the steps of:

a) providing a population of host yeast cells containing a recombinant DNA (r-DNA) YAC library, wherein the host yeast cells are Saccharomycea and the r-DNA YAC library is produced by:
   1) digesting human genomic DNA with a restriction endonuclease selected from the group consisting of ApaI, NsiI and ScaI, thereby producing human DNA fragments and selecting against the occurrence of Alu and L1 repetitive DNA sequences at the termini of the product DNA fragments; and
   2) incorporating human DNA fragments produced in 1) into YACS, thereby producing a human r-DNA YAC library;

b) introducing into the population of host yeast cells containing the r-DNA YAC library a first targeting DNA molecule which is non-replicating in yeast and comprises a selectable marker gene for selection in yeast and a targeting DNA sequence homologous in part to a target r-DNA clone sequence contained in the r-DNA YAC library as a single copy or in low-copy number, under conditions appropriate for viability of the host yeast cells, such that homologous recombination occurs between the targeting DNA sequence and a target r-DNA clone sequence contained in a YAC, whereby the selectable marker gene for selection in yeast and a portion of the targeting DNA sequence in the first targeting DNA molecule are stably incorporated into target r-DNA clone sequence in a YAC;

c) selecting a host yeast cell containing a YAC containing a target r-DNA clone sequence, the target r-DNA clone sequence having the selectable marker gene for selection in yeast and a portion of the targeting DNA sequence in the targeting DNA molecule stably incorporated therein;

d) isolating DNA containing the target r-DNA clone sequence having the selectable marker gene for selection in yeast and a portion of the targeting DNA sequence in tho first targeting DNA molecule stably incorporated therein from the host yeast cell selected in step c) thereby obtaining a first target r-DNA clone sequence;

e) subcloning a terminus of the first target r-DNA clone sequence into a DNA molecule which is non-replicating in the host yeast cell and contains a selectable marker gene for selection in the host yeast cell, thereby producing a second targeting DNA molecule which is non-replicating in the host yeast cell and includes the selectable marker gene for selection in the host yeast cell and the subcloned terminus of the first target r-DNA clone sequence, wherein the subcloned terminus of the first target r-DNA clone sequence is homologous in part to a second target r-DNA clone sequence contained in the r-DNA library;

f) introducing the second targeting DNA molecule into a population of host yeast cells containing a r-DNA library; and g) selecting a host yeast cell containing a second target r-DNA clone sequence having the selectable marker for selection in the host yeast cell and a portion of the subcloned terminus of the first intact target r-DNA clone sequence stably incorporated therein by homologous recombination, thereby obtaining a second intact r-DNA clone sequence with a DNA segment contiguous to the subcloned terminus of the first intact r-DNA clone sequence.

16. The method of claim 15 wherein the first targeting DNA molecule and the second targeting DNA molecule are plasmids.

17. The method of claim 16 wherein the first targeting DNA molecule and the second targeting DNA molecule each have a double-strand break introduced within the targeting sequence.

18. The method of claim 15 wherein the first targeting DNA molecule and the second targeting DNA molecule are linear DNA fragments and the target DNA sequence is disrupted by the insertion of the selectable marker for yeast into the target sequence.

19. The method of claim 15 wherein the second targeting DNA sequence has a double-strand break introduced within the targeting sequence.

20. A method for isolating contiguous DNA segments, comprising the steps of:

a) providing a recombinant DNA (r-DNA) YAC library in a population of host yeast cells, wherein the host yeast cells are Saccharomyces and the r-DNA YAC library is produced by;

1) digesting human genomic DNA with a restriction endonuclease selected from the group consisting of ApaI., NsiI and ScaI, thereby producing human DNA fragments and selecting against the occurrence of Alu and L1 repetitive DNA sequences at the termini of the product DNA fragments; and 2) incorporating human DNA fragments produced in 1) into YACs, thereby producing a human r-DNA YAC library;

b) introducing into the population of host yeast cells containing a r-DNA YAC library a first targeting DNA molecule which is non-replicating in yeast and comprises a selectable marker gene for selection in yeast and a targeting DNA sequence homologous in part to a target r-DNA clone sequence contained in the r-DNA YAC library as a single copy or in low-copy number, under conditions appropriate for viability of host yeast cells, such that homologous recombination occurs between the targeting DNA sequence and a target r-DNA sequence contained in a YAC, whereby the selectable marker gene for selection in yeast and a portion of the targeting DNA sequence in the first targeting DNA molecule are stably incorporated into a target r-DNA clone sequence in a YAC;

c) selecting a host yeast cell containing a YAC containing a target r-DNA clone sequence, the selectable marker gene for selection in yeast and a portion of the targeting DNA sequence in the targeting DNA molecule stably incorporated therein;

d) isolating DNA containing the target r-DNA clone sequence having the selectable marker gene for selection in yeast and a portion of the targeting DNA sequence of the first targeting DNA molecule from the YAC in the host yeast cell selected in step (c), thereby obtaining a first target r-DNA clone sequence;

e) subcloning the terminus of the first r-DNA clone sequence isolated in step d) into a plasmid and introducing into the plasmid a selectable marker gene for selection in the host yeast cell in such a manner that a linear DNA fragment which is non-replicating in the host yeast cell can be isolated, the linear DNA fragment containing the selectable marker gene for selection in the host yeast cell and the terminus of the first r-DNA clone sequence;

f) isolating from the plasmid produced in e) a linear DNA fragment which is non-replicating in the host yeast cell and contains the selectable marker gene for selection in the host yeast cell and the terminus of the first r-DNA clone sequence, referred to as the isolated linear DNA fragment which contains the selectable marker gene for the host yeast cell;

g) introducing into a population of host cells containing a r-DNA library the isolated linear DNA fragment which contains the selectable marker gene for the host yeast cell and the terminus of the first r-DNA clone sequence as a second targeting DNA sequence wherein the terminus of the first r-DNA clone sequence is homologous in part to a second target r-DNA clone sequence contained in the r-DNA library; and h) selecting a transformed host cell containing a second target r-DNA clone having the selectable marker for the host yeast cell and a portion of the second targeting DNA sequence stably incorporated by homologous recombination into the second target r-DNA clone sequence, thereby obtaining a second r-DNA clone sequence with a DNA segment contiguous to the subcloned terminus of the first r-DNA clone sequence.

21. The method of claim 20 wherein the first targeting DNA molecule and the second targeting DNA molecule are plasmids.

22. The method of claim 20 wherein the first targeting DNA molecule and the second targeting DNA molecule each have a double-strand break introduced within the targeting sequence.

23. The method of claim 20 wherein the first targeting DNA molecule and the second targeting DNA molecule are linear DNA fragments and the targeting DNA sequence is disrupted by the insertion of the selectable marker gene for yeast into the targeting DNA sequence.

24. The method of claim 20 wherein the second targeting DNA sequence has a double-strand break introduced within the targeting sequence.

25. A method for isolating contiguous DNA segments, comprising the steps of:

a) providing a first recombinant DNA (r-DNA) YAC library in a first population of host yeast cells, wherein the host yeast cells are Saccharomyces and the YACs of the library comprise two DNA sequences necessary for replication in bacteria, one at each end of the YAC; two different marker genes for selection in bacteria, one at each end of the YAC; and two different marker genes for selection in yeast, one at each end of the YAC, wherein the marker genes for selection in yeast are different from the marker genes for selection in bacteria;

b) introducing into the population of host yeast cells containing a r-DNA YAC library a first targeting DNA molecule which is non-replicating in yeast and comprises a first selectable marker gene for selection in yeast, different from said two different marker genes for selection in yeast, and a first targeting DNA sequence homologous in part to a first target r-DNA clone sequence contained in the r-DNA YAC library as a single copy or in low-copy humber, under conditions appropriate for viability of the host yeast cells, such that homologous recombination occurs between the first targeting DNA sequence and the first target r-DNA clone sequence, whereby the first selectable marker gene and a portion of the first targeting DNA sequence present in the first targeting DNA molecule are stably incorporated into a YAC containing the first target r-DNA clone sequence;

c) selecting a first host yeast cell containing a first YAC containing the target r-DNA clone sequence having stably incorporated therein by homologous recombination the first selectable marker gene and a portion of the first targeting DNA sequence present in the first targeting DNA molecule;

d) isolating DNA from the host yeast cell selected in step c);

e) digesting the isolated DNA with a restriction endonuclease that releases a DNA fragment from an end of the YAC containing the first target r-DNA clone sequence, which DNA fragment comprises one each: of said DNA sequences for replication in bacteria of said two different marker genes for selection in bacteria; and of said two different marker genes for selection in yeast, which is a second selectable marker gene for selection in yeast; and a terminus of said first r-DNA clone sequence, thereby producing a rescued DNA fragment;

f) recovering the rescued DNA fragment as a plasmid in Escherichia coli, wherein said rescued DNA fragment lacks telomeric and centromere sequences derived from the YAC of the first R-DNA YAC library, wherein said terminus of the first r-DNA clone sequence is a second targeting DNA sequences;

g) transforming a second population of Sacharomyces host yeast cells which contains a second r-DNA YAC library with the rescued DNA fragment; wherein said selectable yeast marker gene is selectable in the second population of host yeast cells and said second targeting DNA sequences is homologous in part to a second target r-DNA clone sequence present in the second r-DNA YAC library; and h) selecting a second transformed host yeast cell containing a second YAC containing a second target r-DNA clone sequence having the second selectable marker gene and a portion of the second targeting DNA sequence stably incorporated by homologous recombination into the second target r-DNA clone sequence, thereby obtaining a second YAC having a DNA segment contiguous to the terminus of the first YAC.

26. The method of claim 25 wherein the first targeting plasmid has a double-strand break introduced within the targeting sequence.

27. The method of claim 25 wherein the second targeting DNA sequence has a double-strand break introduced within the targeting sequence.

28. The method of claim 25 wherein the first r-DNA YAC library and the second r-DNA YAC library are produced by a method of producing a human recombinant DNA (r-DNA) library, wherein the library comprises r-DNA clone inserts and there is a bias against the occurrence of Alu and L1 repetitive DNA sequences at the termini of the r-DNA clone inserts, comprising a) digesting human genomic DNA with a restriction endonuclease selected from the group consisting of ApaI, XsI and ScaI, thereby producing human DNA fragments and selecting against the occurrence of Alu and L1 repetitive DNA sequences at the termini of the product DNA fragments; and b) incorporating human DNA fragments produced in a) into YACs, thereby producing a human r-DNA YAC library.

29. Plasmid pTKENDA.

* * * * *

UNITED STATES PATENT AND TRADEMARK OFFICE
CERTIFICATE OF CORRECTION

PATENT NO. : 5,783,385
DATED : July 21, 1998
INVENTOR(S) : Douglas A. Treco and Allan M. Miller It is certified that error appears in the above-identified patent and that said Letters Patent is hereby corrected as shown below:

Column 30, line 54, delete "Saccharomyceo" and insert --Saccharomyces--.
      Column 31, line 54, delete "Saccharomycea" and insert --Saccharomyces--.
      Column 32, line 22, delete "tho" and insert --the--.
      Column 34, line 29, delete "cach" and insert --each--; line 42, delete "humber" and insert --number,--;
      DNA--; line 64, delete "bacteria" and insert --bacteria;--.
      Column 35, line 6, delete "R-DNA" and insert --r-DNA--; line 8, delete "sequences;" and insert --sequence;--.

Signed and Sealed this

Sixteenth Day of May, 2000

Attest:

Q. TODD DICKINSON

*Attesting Officer*        *Director of Patents and Trademarks*